United States Patent
Briggs et al.

(10) Patent No.: US 12,071,636 B2
(45) Date of Patent: Aug. 27, 2024

(54) PASTEURELLA MULTOCIDA STRAINS AND VACCINES HAVING HYAC AND NANP DELETIONS

(71) Applicant: The United States of America, as represented by the Secretary of Agriculture, Washington, DC (US)

(72) Inventors: Robert E Briggs, Boone, IA (US); Fred M Tatum, Nevada, IA (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/478,023

(22) Filed: Sep. 17, 2021

(65) Prior Publication Data
US 2022/0098558 A1    Mar. 31, 2022

Related U.S. Application Data

(60) Provisional application No. 63/085,495, filed on Sep. 30, 2020.

(51) Int. Cl.
| | |
|---|---|
| *C12N 9/16* | (2006.01) |
| *A61K 39/102* | (2006.01) |
| *C12N 9/04* | (2006.01) |
| *A61K 39/00* | (2006.01) |

(52) U.S. Cl.
CPC .......... *C12N 9/0006* (2013.01); *A61K 39/102* (2013.01); *C12N 9/16* (2013.01); *C12Y 101/01022* (2013.01); *C12Y 301/03029* (2013.01); *A61K 2039/522* (2013.01); *A61K 2039/552* (2013.01)

(58) Field of Classification Search
CPC ........ C12N 9/0006; C12N 2760/00034; C12N 2770/32134; C12N 9/16; C12Y 101/01022; A61P 31/04
USPC ............................................ 424/201.1, 255.1
See application file for complete search history.

(56) References Cited

U.S. PATENT DOCUMENTS

| | | |
|---|---|---|
| 7,763,262 B2 | 7/2010 | Lowery et al. |
| 10,603,371 B2 | 3/2020 | Lawrence et al. |
| 2008/0241192 A1 | 10/2008 | Kumar et al. |
| 2015/0125487 A1 | 5/2015 | Lawrence et al. |
| 2017/0319678 A1 | 11/2017 | Briggs et al. |
| 2018/0015157 A1 | 1/2018 | Lawrence et al. |

FOREIGN PATENT DOCUMENTS

| | | | |
|---|---|---|---|
| EP | WO03/086277 | * | 10/2003 |

OTHER PUBLICATIONS

Kisselev L., (Structure, 2002, vol. 10: 8-9.*
Witkowski et al., (Biochemistry 38:11643-11650, 1999.*
BWhisstock et al., (Quarterly Reviews of Biophysics 2003, vol. 36 (3): 307-340.*
Devos et al., (Proteins: Structure, Function and Genetics, 2000, vol. 41: 98-107.*
Briggs R.G. and Tatum F., "Generation and molecular characterization of new temperature-sensitive plasmids intended for genetic engineering of Pasteurellaceae" Appl. Environ. Microbiol. 2005, vol. 71, pp. 7187-7195.
Chung J. Y, et al., "Role of capsule in the pathogenesis of fowl cholera caused by Pasteurella multocida serogroup A," Infect. Immun., Apr. 2001, vol. 69, No. 4, pp. 2487-2492.
Fuller T. et al., "Identification of Pasteurella multocida virulence genes in a septicemic mouse model using signature-tagged mutagenesis," Microb. Pathog. 2000, vol. 29, pp. 25-38.
Griffin, D., "Bovine pasteurellosis and other bacterial infections of the respiratory tract," Vet. Clin. North Am. Food Anim. Pract., 2010, vol. 26, pp. 57-71.
Snipes K. et al., "Fate of Pasteurella multocida in the blood vascular system of turkeys following intravenous noculation: comparison of an encapsulated, virulent strain with its avirulent, acapsular variant," Avian Dis., 1986, vol. 31: 254-259.
Steen, J. A. et al., "Fis is essential for capsule production in Pasteurella multocida and regulates expression of other Important virulence factors", PLoS Pathogens, 2010, vol. 6, No. 2, Article No. e1000750 (pp. 1-14).
Smith H., et al., "Sialylation of neisserial lipopolysaccharide: a major influence on pathogenicity," Microb. Path., Dec. 1995, vol. 19, No. 6, pp. 365-377.
Steenbergen S., et al., "Sialic acid metabolism and systemic pasteurellosis," Infect. Immun. Mar. 2005, vol. 73, No. 3, pp. 1284-1294.
Tatum F. M., et al., "Sialic acid uptake is necessary for virulence of Pasteurella multocida in turkeys," Microb. Pathog., 2009, vol. 46, pp. 337-344.
Vimr E. and Lichtensteiger C., "To sialylate, or not to sialylate: that is the question," Trends Microbiol., Jun. 2002, vol. 10 No. 6, pp. 254-257.
Yates, W. D., "A review of infectious bovine rhinotracheitis, shipping fever pneumonia and viral-bacterial synergism in respiratory disease of cattle," Can. J. Comp. Med., 1982, vol. 46, No. 3, pp. 225-263.
International Search Report on PCT/US2021/051937 dated Jan. 13, 2022.
Written Opinion of he International Searching Authority on PCT/US2021/051937 dated Jan. 13, 2022.
International Preliminary Report on Patentability on PCT/US2021/051937 dated Mar. 28, 2023.

* cited by examiner

*Primary Examiner* — Robert B Mondesi
*Assistant Examiner* — Mohammad Y Meah
(74) *Attorney, Agent, or Firm* — John Fado; Maria Restrepo-Hartwig

(57) ABSTRACT

The present invention provides novel attenuated *Pasteurella multocida* strains that may be used, in live or killed form, to formulate vaccines that are highly protective against *P. multocida* infection in bovines, other mammals, and in birds. The present invention also identifies the combination of nanP and hyaC gene mutations as key to the provision of such vaccines. When appropriately formulated, antigenic material of numerous other bovine pathogens may be combined with the live attenuated *Pasteurella multocida* strains, to make effective combination vaccines.

10 Claims, 6 Drawing Sheets

Specification includes a Sequence Listing.

SEQUENCE LISTING

<160> NUMBER OF SEQ ID NOS: 22

<210> SEQ ID NO 1
<211> LENGTH: 984
<212> TYPE: DNA
<213> ORGANISM: Pasteurella multocida

<400> SEQUENCE: 1

```
atgaaattta aaaaactact acttgcatct ttatgtttag gtgtttcagc ttctgtattt      60
gcagcagatt acgatcttaa attcggtatg gttgcgggtc caagctcaaa cgaatataaa     120
gcagtagaat tctttgcgaa agaagtgaaa gaaaaatcca atggcaaaat tgatgtggct     180
attttcccta gctcacagtt aggtgatgac cgtgtgatga ttaaacaatt aaaagacggt     240
gcattagact ttacgttagg tgaatcagca cgtttccaaa tttacttccc agaagcagaa     300
gtatttgcgt tgccttatat gattcctaat tttgaaacct ctaaaaaagc gttgctcgac     360
acaaaatttg gtcaaggttt attgaaaaaa attgataaag agttaaacgt acaagtgtta     420
tctgtggcgt ataacggtac acgtcaaaca acttctaacc gtgcaatcaa cagcattgaa     480
gacatgaaag ggttaaaatt acgtgtacct aacgcggcaa ccaaccttgc ttatgcaaaa     540
tacgtgggtg cagcgccaac accaatggca ttctctgaag tttaccttgc gcttcaaaca     600
aactctgtgg atggtcaaga aaacccatta ccgacaatcc aagcacaaaa attctatgaa     660
gtacaaaaat acttagcgtt aactaaccac atcttaaatg accaacttta cttaatcagt     720
aacgatacgt tggcagattt accagaagat ttacaaaaag tggttaaaga tgcagcagcg     780
aaagccgctg aatatcacac taaactcttc gttgacggtg agaacagctt agttgaattc     840
ttcaaaagtc aaggtgtgac agtcacacaa ccagacttaa aaccatttaa agcagcactt     900
acaccatact atgatgaata tctcaagaaa aatggtgaag tcggtaaaat ggcgattgaa     960
gaaatttcta atctcgctaa ataa                                            984
```

<210> SEQ ID NO 2
<211> LENGTH: 327

```
<212> TYPE: PRT
<213> ORGANISM: Pasteurella multocida

<400> SEQUENCE: 2

Met Lys Phe Lys Lys Leu Le

```
gcagcagatt acgatcttaa attcggtatg gttgcgggtc caagctcaaa cgaatataaa      120
gcagtagaat tcttcaaaag tcaaggtgtg acagtcacac aaccagactt aaaaccattt      180
aaagcagcac ttacaccata ctatgatgaa tatctcaaga aaatggtga agtcggtaaa       240 atggcgattg aagaaatttc taatctcgct aaataa                                276

<210> SEQ ID NO 4
<211> LENGTH: 90
<212> TYPE: PRT
<213> ORGANISM: Artificial Sequence
<220> FEATURE:
<223> OTHER INFORMATION: Chemically Synthesized

<400> SEQUENCE: 4

Met Lys Phe Lys Lys Leu Leu Leu Ala Ser Leu Cys Leu Gly Val Ser
1               5                   10                  15

Ala Ser Val Phe Ala Ala Asp Tyr Asp Leu Lys Phe Gly Met Val Ala
            20                  25                  30

Gly Pro Ser Ser Asn Glu Tyr Lys Ala Val Glu Phe Lys Ser Gln Gly
        35                  40                  45

Val Thr Val Thr Gln Pro Asp Leu Lys Pro Phe Lys Ala Ala Leu Thr
    50                  55                  60

Pro Tyr Tyr Asp Glu Tyr Leu Lys Lys Asn Gly Glu Val Gly Lys Met
65                  70                  75                  80

Ala Ile Glu Glu Ile Ser Asn Leu Ala Lys
                85                  90

<210> SEQ ID NO 5
<211> LENGTH: 2852
<212> TYPE: DNA
<213> ORGANISM: Artificial Sequence
<220> FEATURE:
<223> OTHER INFORMATION: Chemically Synthesized

<400> SEQUENCE: 5
gcggatgtga tagttttgac atattaactc cagtctaaat ttatcaaaag aagattgact      60
ccaatttgca taggttaatc ttagaattaa aaaataacaa ccaaaataat aaaaatttga      120
gatctttgtc gcatatttat tcatagggaa tagacagctt aatttttagtt atgatttgtc     180 aatccttgct atttttgtg tttgctggtt tgcgatacac tgttctaata ttgctttgag       240
cacttgataa ccttgctcat taaaatgtaa tccgtcggta caaggcgta atccagttc        300 accgttagaa tcacaaaagt attttttgtgt ttcaacgtaa gtcacgtctg acggacaatg     360
ttgttttaaa taggtattga gcctgtgaat ttgtgcgtta gtgaccgtat taatctgatt      420
gaccggtgtg gcttctaata aaagtagtg ggacgtagga gaatggtgt gtaggtgagt       480 cagaatgtca tttaactatc gcatgacttg cgccggtgaa tacgtttctt ccttacaaat     540
atcattgacg cctaaaaaaa gaaaaacaga ttgtccaagt tgttgaatcc gtttaggttt     600
aacgataaca tccaaatatt gtcgcgtact gacgccagaa agtcctaaat tggcgacggt     660
ttgtcccgct aattgaggtg tgcctgctac ctgttcgtcc cacatgtcaa aaagtgaatg     720
accaattaag ctgatattgg caggtttgga aaattccgcc attttgctct gatagcgttg    780
ataaatatcc tgatcactta gcatgtgtgg acctctattt tgaaataaaa cgctaagtat    840
tatataaaac ctgatatgcc ggtaaacagt aaacttatct tccgtagggg taaatattca    900
attttgtgac gaacctatca tttatgaaat aaaacttcat tttctatata aaaaatagtt    960
```

-continued

| | | |
|---|---|---|
| ttttcactttt agaatgccaa acgtgtgaaa tttatttcat catcatttta acgtaatccc | 1020 | |
| aacgtaaccca atagaggaga actcataatg aaatttaaaa aactactact tgcatcttta | 1080 | |
| tgtttaggtg tttcagcttc tgtatttgca gcagattacg atcttaaatt cggtatggtt | 1140 | |
| gcgggtccaa gctcaaacga atataaagca gtagaattct ttgcgaaaga agtgaaagaa | 1200 | |
| aaatccaatg gcaaaattga tgtggctatt ttccctagct cacagttagg tgatgaccgt | 1260 | |
| gtgatgatta acaattaaa agacggtgca ttagacttta cgttaggtga atcagcacgt | 1320 | |
| ttccaaattt acttcccaga agcagaagta tttgcgttgc cttatatgat tcctaatttt | 1380 | |
| gaaacctcta aaaagcgtt gctcgacaca aatttggtc aaggtttatt gaaaaaaatt | 1440 | |
| gataaagagt taaacgtaca agtgttatct gtggcgtata acggtacacg tcaaacaact | 1500 | |
| tctaaccgtg caatcaacag cattgaagac atgaaagggt taaaattacg tgtacctaac | 1560 | |
| gcggcaacca accttgctta tgcaaaatac gtgggtgcag cgccaacacc aatggcattc | 1620 | |
| tctgaagttt accttgcgct tcaaacaaac tctgtggatg gtcaagaaaa cccattaccg | 1680 | |
| acaatccaag cacaaaaatt ctatgaagta caaaaatact tagcgttaac taaccacatc | 1740 | |
| ttaaatgacc aactttactt aatcagtaac gatacgttgg cagatttacc agaagattta | 1800 | |
| caaaaagtgg ttaaagatgc agcagcgaaa gccgctgaat atcacactaa actcttcgtt | 1860 | |
| gacggtgaga acagcttagt tgaattcttc aaaagtcaag gtgtgacagt cacacaacca | 1920 | |
| gacttaaaac catttaaagc agcacttaca ccatactatg atgaatatct caagaaaaat | 1980 | |
| ggtgaagtcg gtaaaatggc gattgaagaa atttctaatc tcgctaaata aatatagtaa | 2040 | |
| ccttatccct gcgccttaag ggataaggtt ccttttatt gggttgtctt gaggtatcta | 2100 | |
| tgaaaataat aaataaatta gaagagtgga ttggcggtgt gctattcatt ggaattttct | 2160 | |
| taattctgtt agcacaaatc attgctcgtc aagtgtttca gtcaccgttt atttggagtg | 2220 | |
| aagaactcgc aagattgcta tttatctatg tcgggctact tggtatcagc atgggtatcc | 2280 | |
| gtagtcagca gcatgtttat attgattttt taactaactt tatgcccgag aaagtgagaa | 2340 | |
| aggtgacaaa ctcctttgtt caagttctca tctttatttc catcattatt ttcattcatt | 2400 | |
| taggctttaa agtttggatc gactccagtt ttaaaatgga agcgttaact gctttcgctt | 2460 | |
| cagatttaat tgggcgcgag acgattgtgc ctgaaaaatg gatgtatgcg gcattgcctt | 2520 | |
| ttatttcttg tttaatgtta ttccgctttt tccaagcgca agttgaaaat tatagaaata | 2580 | |
| agttaagtta tattcctgtc acggcatttg tgattggtgc ggtcattatt tttgcgattt | 2640 | |
| tattgattga gccagattgg tataaagtcc tccgtatttc aaattatgtg aaatttggtg | 2700 | |
| gtgatgcagt gtatatcaca ttagtgattt ggcttgtcat tatgtttgtg ggaaccccgg | 2760 | |
| taggttggtc attatttatt gcgacgttgc tttattttgc gatgacgcgt tggaatattg | 2820 | |
| ttaactcggc atcaaccaag ctcaccgaca gt | 2852 | |

<210> SEQ ID NO 6
<211> LENGTH: 1793
<212> TYPE: DNA
<213> ORGANISM: Artificial Sequence
<220> FEATURE:
<223> OTHER INFORMATION: Chemically Synthesized

<400> SEQUENCE: 6

| | | |
|---|---|---|
| atgttgataa gaatcatctt acaccagata tcaaaaaaga aatactagcc ttctatcata | 60 | |
| aacatcaagt gaatatttta ctaaataatg atatctcata ttcacgagt aatagattaa | 120 | |
| taaaaactga ggcgcattta agtaatatta ataaattaag tcagttaaat ctaaattgtg | 180 | |

```
aatacatcat ttttgataat catgacagcc tattcgttaa aaatgacagc tatgcttata      240
tgaaaaaata tgatgtcggc atgaatttct cagcattaac acatgattgg atcgagaaaa      300
tcaatgcgca tccaccattt aaaaagctca ttaaaactta ttttaatgac aatgacttaa      360
aaagtatgaa tgtgaaaggg gcatcacaag gtatgtttat gacgtatgcg ctagcgcatg      420
agcttctgac gattattaaa gaagtcatca catcttgcca gtcaattgat agtgtgccag      480
aatataacac tgaggatatt tggttccaat ttgcactttt aatcttagaa aagaaaaccg      540
gccatgtatt aataaaaca tcgaccctga cttatatgcc ttgggaacga aaattacaat       600
ggacaaatga acaaattgaa agtgcaaaaa gaggagaaaa tatacctgtt aacaagttca      660
ttattaatag tataactcta taaaacactt gcattttatt aaaaataaaa tcctataata      720
tttgcagttt aaataaagga taaaaaatga agaaaattac aattgctggg gctggctatg      780
ttggtttatc caatgcagta ttattagctc aacaccacaa tgtgatctta ttagatattg      840
atcaaaataa agttgattta attaataata aaaaatcgcc catcacagat aaagaaatcg      900
aagatttctt acaaaataaa tcactgacaa tgatggcaac aacagataaa gaagtggcat      960
taaaaaacgc agactttgtc atcatcgcaa cgccactgca gcaagtttcg gctatggcgg     1020
ttattgttta cccaaagaca ctaaacagtt actggctaac tatgctgacg tacctcaaaa     1080
tctcattgaa gccattgtca aatctaatga accagaaaa cgtttcatta ctcatgatgt      1140
attaaataag aaacctaaaa ctgttggtat ttatcgttta atcatgaagt caggttctga     1200
taacttcaga gcttctgcta ttctcgatat tatgccgcat ctcaaagaaa acggtgttga     1260
gattgtgatt tatgagccaa ccttaaatca acaggcattt gaggactacc ccgttattaa     1320
tcaactctct gaatttatta atcgctctga tgtcattctc gctaatcgtt ctgagccaga     1380
tttaaatcaa tgttcccata aaatctatac aagagatatt tttggcggtg atgcttaacc     1440
tgtttaaaat cataaaaaag tatgtgcata ttcaatcttt attacacaaa aaagaatatg     1500
ccttacttta tgctaaatac ataaaccagc tttctatcaa ccagcaggct tatgttattt     1560
gtcaactcaa actctatgat ctctttctga ttgatcctaa atggagccac tctgtttttt     1620
tccagttagg attaattgct cgtggacacg atcatgatag cgatgaagtg gtacgtcgtt     1680
tgatcacttg cactgatttt agcaaaaata agcagttaat cctttctcaa ttacttgctt     1740
attcacctca aattgcaaca acattatgtc cacagacata tcgttatcgt gcg            1793

<210> SEQ ID NO 7
<211> LENGTH: 2144
<212> TYPE: DNA
<213> ORGANISM: Artificial Sequence
<220> FEATURE:
<223> OTHER INFORMATION: Chemically Synthesized

<400> SEQUENCE: 7
gcggatgtga tagttttgac atattaactc cagtctaaat ttatcaaaag aagattgact       60
ccaatttgca taggttaatc ttagaattaa aaaataacaa ccaaaataat aaaaatttga      120
gatctttgtc gcatatttat tcatagggaa tagacagctt aattttagtt atgatttgtc      180
aatccttgct attttttgtg tttgctggtt tgcgatacac tgttctaata ttgctttgag      240
cacttgataa ccttgctcat taaaatgtaa tccgtcggta caaggcgta aatccagttc       300 accgttagaa tcacaaaagt attttttgtgt ttcaacgtaa gtcacgtctg acggacaatg      360
ttgttttaaa taggtattga gcctgtgaat ttgtgcgtta gtgaccgtat taatctgatt       420
```

```
gaccggtgtg gcttctaata aaaagtagtg ggacgtagga gaaatggtgt gtaggtgagt      480
cagaatgtca tttaactatc gcatgacttg cgccggtgaa tacgtttctt ccttacaaat      540
atcattgacg cctaaaaaaa gaaaaacaga ttgtccaagt tgttgaatcc gtttaggttt      600
aacgataaca tccaaatatt gtcgcgtact gacgccagaa agtcctaaat tggcgacggt      660
ttgtcccgct aattgaggtg tgcctgctac ctgttcgtcc cacatgtcaa aaagtgaatg      720
accaattaag ctgatattgg caggtttgga aaattccgcc attttgctct gatagcgttg      780
ataaatatcc tgatcactta gcatgtgtgg acctctattt tgaaataaaa cgctaagtat      840
tatataaaac ctgatatgcc ggtaaacagt aaacttatct tccgtagggg taaatattca      900
attttgtgac gaacctatca tttatgaaat aaaacttcat tttctatata aaaaatagtt      960
ttttcacttt agaatgccaa acgtgtgaaa tttatttcat catcatttta acgtaatccc     1020
aacgtaacca atagaggaga actcataatg aaatttaaaa aactactact tgcatcttta     1080
tgtttaggtg tttcagcttc tgtatttgca gcagattacg atcttaaatt cggtatggtt     1140
gcgggtccaa gctcaaacga atataaagca gtagaattct tcaaaagtca aggtgtgaca     1200
gtcacacaac cagacttaaa accatttaaa gcagcactta caccatacta tgatgaatat     1260
ctcaagaaaa atggtgaagt cggtaaaatg gcgattgaag aaatttctaa tctcgctaaa     1320
taaatatagt aaccttatcc ctgcgcctta agggataagg ttccttttta ttgggttgtc     1380
ttgaggtatc tatgaaaata ataaataaat tagaagagtg gattggcggt gtgctattca     1440
ttggaatttt cttaattctg ttagcacaaa tcattgctcg tcaagtgttt cagtcaccgt     1500
ttatttggag tgaagaactc gcaagattgc tatttatcta tgtcgggcta cttggtatca     1560
gcatgggtat ccgtagtcag cagcatgttt atattgattt tttaactaac tttatgcccg     1620
agaaagtgag aaaggtgaca aactcctttg ttcaagttct catctttatt tccatcatta     1680
ttttcattca tttaggcttt aaagtttgga tcgactccag ttttaaaatg gaagcgttaa     1740
ctgctttcgc ttcagattta attgggcgcg agacgattgt gcctgaaaaa tggatgtatg     1800
cggcattgcc ttttatttct tgtttaatgt tattccgctt tttccaagcg caagttgaaa     1860
attatagaaa taagttaagt tatattcctg tcacggcatt tgtgattggt gcggtcatta     1920
tttttgcgat tttattgatt gagccagatt ggtataaagt cctccgtatt tcaaattatg     1980
tgaaatttgg tggtgatgca gtgtatatca cattagtgat ttggcttgtc attatgtttg     2040
tgggaacccc ggtaggttgg tcattattta ttgcgacgtt gctttatttt gcgatgacgc     2100
gttggaatat tgttaactcg gcatcaacca agctcaccga cagt                      2144
```

<210> SEQ ID NO 8
<211> LENGTH: 1170
<212> TYPE: DNA
<213> ORGANISM: Pasteurella multocida

<400> SEQUENCE: 8

```
atgaagaaaa ttacaattgc tggggctggc tatgttggtt tatccaatgc agtattatta       60
gctcaacacc acaatgtgat cttattagat attgatcaaa ataaagttga tttaattaat      120
aataaaaaat cgcccatcac agataaagaa atcgaagatt tcttacaaaa taaatcactg      180
acaatgatgg caacaacaga taagaagtg gcattaaaaa acgcagactt tgtcatcatc      240
gcaacgccaa cagactataa taccgaaaca ggttatttta atacatccac tgttgaagct      300
gtcattgaac aaacccttc aatcaatcca caagcaacga ttattataaa atcaacgatt      360
cccgttggtt ttaccgaaaa aatgcgtgag aaatttaata ccccaaatct tatcttttca      420
```

```
cctgaatttc taagagaggg aaaagcccctt tacgataatt tgtatccaag cagaattatt      480
gttggcagta cttcttatca agcaaaagta tttgccgata tgttaacaca gtgtgccaga      540
aaaaaagatg taactgtttt atttacacac aatactgagg ccgaagctgt taaattattt     600
gcaaatacgt atctcgcaat gcgagttgcc ttttttaatg aattagatac ttatgcgagt      660
cttcaccatt taaatacaaa agacattatc aatggtattt ctactgatcc tcgcattggt      720
acacactaca ataacccaag tttcggctat ggcggttatt gtttacccaa agacactaaa      780
cagttactgg ctaactatgc tgacgtacct caaaatctca ttgaagccat tgtcaaatct      840
aatgaaacca gaaaacgttt cattactcat gatgtattaa ataagaaacc taaaactgtt      900
ggtatttatc gtttaatcat gaagtcaggt tctgataact tcagagcttc tgctattctc      960
gatattatgc cgcatctcaa agaaaacggt gttgagattg tgatttatga gccaacctta     1020
aatcaacagg catttgagga ctaccccgtt attaatcaac tctctgaatt tattaatcgc     1080
tctgatgtca ttctcgctaa tcgttctgag ccagatttaa atcaatgttc ccataaaatc     1140
tatacaagag atattttggg cggtgatgct                                       1170
```

<210> SEQ ID NO 9
<211> LENGTH: 390
<212> TYPE: PRT
<213> ORGANISM: Pasteurella multocida

<400> SEQUENCE: 9

```
Met Lys Lys Ile Thr Ile Ala Gly Ala Gly Tyr Val Gly Leu Ser Asn
1

```
Thr His Tyr Asn Asn Pro Ser Phe Gly Tyr Gly Gly Tyr Cys Leu Pro
            245                 250                 255

Lys Asp Thr Lys Gln Leu Leu Ala Asn Tyr Ala Asp Val Pro Gln Asn
            260                 265                 270

Leu Ile Glu Ala Ile Val Lys Ser Asn Glu Thr Arg Lys Arg Phe Ile
            275                 280                 285

Thr His Asp Val Leu Asn Lys Lys Pro Lys Thr Val Gly Ile Tyr Arg
            290                 295                 300

Leu Ile Met Lys Ser Gly Ser Asp Asn Phe Arg Ala Ser Ala Ile Leu
305                 310                 315                 320

Asp Ile Met Pro His Leu Lys Glu Asn Gly Val Glu Ile Val Ile Tyr
            325                 330                 335

Glu Pro Thr Leu Asn Gln Gln Ala Phe Glu Asp Tyr Pro Val Ile Asn
            340                 345                 350

Gln Leu Ser Glu Phe Ile Asn Arg Ser Asp Val Ile Leu Ala Asn Arg
            355                 360                 365

Ser Glu Pro Asp Leu Asn Gln Cys Ser His Lys Ile Tyr Thr Arg Asp
            370                 375                 380

Ile Phe Gly Gly Asp Ala
385                 390

<210> SEQ ID NO 10
<211> LENGTH: 2500
<212> TYPE: DNA
<213> ORGANISM: Artificial Sequence
<220> FEATURE:
<223> OTHER INFORMATION: Chemically Synthesized

<400> SEQUENCE: 10
attattgaat ataataaaaa tatattcgtt attgttctac atgttgataa gaatcatctt      60
acaccagata tcaaaaaaga aatactagcc ttctatcata acatcaagt gaatatttta     120 ctaaataatg atatctcata ttacacgagt aatagattaa taaaaactga ggcgcattta    180
agtaatatta ataaattaag tcagttaaat ctaaattgtg aatacatcat ttttgataat    240
catgacagcc tattcgttaa aaatgacagc tatgcttata tgaaaaaata tgatgtcggc    300
atgaatttct cagcattaac acatgattgg atcgagaaaa tcaatgcgca tccaccattt    360
aaaaagctca ttaaaactta ttttaatgac aatgacttaa aagtatgaa tgtgaaaggg     420 gcatcacaag gtatgtttat gacgtatgcg ctagcgcatg agcttctgac gattattaaa    480
gaagtcatca catcttgcca gtcaattgat agtgtgccag aatataacac tgaggatatt    540
tggttccaat ttgcactttt aatcttagaa aagaaaccg gccatgtatt aataaaaaca     600
tcgaccctga cttatatgcc ttgggaacga aaattacaat ggacaaatga acaaattgaa    660
agtgcaaaaa gaggagaaaa tatacctgtt aacaagttca ttattaatag tataactcta    720
taaaacactt gcattttatt aaaaataaaa tcctataata tttgcagttt aaataaagga    780
taaaaaatga agaaaattac aattgctggg gctggctatg ttggtttatc caatgcagta    840
ttattagctc aacaccacaa tgtgatctta ttagatattg atcaaaataa agttgattta    900
attaataata aaaaatcgcc catcacagat aaagaaatcg aagatttctt acaaaataaa    960
tcactgacaa tgatggcaac aacagataaa gaagtggcat taaaaaacgc agactttgtc   1020
atcatcgcaa cgccaacaga ctataatacc gaaacaggtt attttaatac atccactgtt   1080
gaagctgtca ttgaacaaac ccttcaatc aatccacaag caacgattat tataaaatca    1140
```

```
acgattcccg ttggttttac cgaaaaaatg cgtgagaaat ttaataccccc aaatcttatc   1200 ttttcacctg aatttctaag agagggaaaa gcccttttacg ataatttgta tccaagcaga   1260
attattgttg gcagtacttc ttatcaagca aaagtatttg ccgatatgtt aacacagtgt   1320
gccagaaaaa aagatgtaac tgttttattt acacacaata ctgaggccga agctgttaaa   1380
ttatttgcaa atacgtatct cgcaatgcga gttgccttttt ttaatgaatt agatacttat   1440
gcgagtcttc accatttaaa tacaaaagac attatcaatg gtatttctac tgatcctcgc   1500
attggtacac actacaataa cccaagtttc ggctatggcg gttattgttt acccaaagac   1560
actaaacagt tactggctaa ctatgctgac gtacctcaaa atctcattga agccattgtc   1620
aaatctaatg aaaccagaaa acgtttcatt actcatgatg tattaaataa gaaacctaaa   1680
actgttggta tttatcgttt aatcatgaag tcaggttctg ataacttcag agcttctgct   1740
attctcgata ttatgccgca tctcaaagaa aacggtgttg agattgtgat ttatgagcca   1800
accttaaatc aacaggcatt tgaggactac cccgttatta atcaactctc tgaatttatt   1860
aatcgctctg atgtcattct cgctaatcgt tctgagccag atttaaatca atgttcccat   1920
aaaatctata caagagatat ttttggcggt gatgcttaac ctgttttaaaa tcataaaaaa   1980 gtatgtgcat attcaatctt tattacacaa aaaagaatat gccttacttt atgctaaata   2040
cataaaccag ctttctatca accagcaggc ttatgttatt tgtcaactca aactctatga   2100
tctctttctg attgatccta aatggagcca ctctgttttt ttccagttag gattaattgc   2160
tcgtggacac gatcatgata gcgatgaagt ggtacgtcgt ttgatcactt gcactgattt   2220
tagcaaaaat aagcagttaa tcctttctca attacttgct tattcacctc aaattgcaac   2280
aacattatgt ccacagacat atcgttatcg tgcgctatat ctctcattac tagcgaattt   2340
aaaagacttt gttcgtttaa aagaagaact caataagttg ccgtcatgtg tgttaaagaa   2400
tacacctcat tactgtttgt tacagaattt tgtcgaaaaa gaaacagca agaaattaga   2460 gaacattaat caatttcttt acttttataa acttggagaa                          2500
```

<210> SEQ ID NO 11
<211> LENGTH: 132
<212> TYPE: PRT
<213> ORGANISM: Artificial Sequence
<220> FEATURE:
<223> OTHER INFORMATION: Chemically Synthesized

<400> SEQUENCE: 11

```
Met Lys Lys Ile Thr Ile Ala Gly Ala Gly Tyr Val Gly Leu Ser Asn
1               5                   10                  15

Ala Val Leu Leu Ala Gln His His Asn Val Ile Leu Leu Asp Ile Asp
                20                  25                  30

Gln Asn Lys Val Asp Leu Ile Asn Asn Lys Lys Ser Pro Ile Thr Asp
            35                  40                  45

Lys Glu Ile Glu Asp Phe Leu Gln Asn Lys Ser Leu Thr Met Met Ala
        50                  55                  60

Thr Thr Asp Lys Glu Val Ala Leu Lys Asn Ala Asp Phe Val Ile Ile
65                  70                  75                  80

Ala Thr Pro Leu Gln Gln Val Ser Ala Met Ala Val Ile Val Tyr Pro
                85                  90                  95

Lys Thr Leu Asn Ser Tyr Trp Leu Thr Met Leu Thr Tyr Leu Lys Ile
                100                 105                 110

Ser Leu Lys Pro Leu Ser Asn Leu Met Lys Pro Glu Asn Val Ser Leu
            115                 120                 125
```

Leu Met Met Tyr
    130

<210> SEQ ID NO 12
<211> LENGTH: 683
<212> TYPE: DNA
<213> ORGANISM: Artificial Sequence
<220> FEATURE:
<223> OTHER INFORMATION: Chemically Synthesized

<400> SEQUENCE: 12
atgaagaaaa ttacaattgc tggggctggc tatgttggtt tatccaatgc agtattatta      60
gctcaacacc acaatgtgat cttattagat attgatcaaa ataaagttga tttaattaat     120
aataaaaaat cgcccatcac agataaagaa atcgaagatt tcttacaaaa taatcactg      180 acaatgatgg caacaacaga taaagaagtg cattaaaaa acgcagactt tgtcatcatc      240
gcaacgccac aagtttcggc tatggcggtt attgtttacc caaagacact aaacagttac     300
tggctaacta tgctgacgta cctcaaaatc tcattgaagc cattgtcaaa tctaatgaaa     360
ccagaaaacg tttcattact catgatgtat taaataagaa acctaaaact gttggtattt     420
atcgtttaat catgaagtca ggttctgata acttcagagc ttctgctatt ctcgatatta     480
tgccgcatct caaagaaaac ggtgttgaga ttgtgattta tgagccaacc ttaaatcaac     540
aggcatttga ggactacccc gttattaatc aactctctga atttattaat cgctctgatg     600
tcattctcgc taatcgttct gagccagatt taaatcaatg ttcccataaa atctatacaa     660
gagatatttt tggcggtgat gct                                              683

<210> SEQ ID NO 13
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 13
aaaggatccg cggatgtgat agttttgaca t                                     31

<210> SEQ ID NO 14
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 14
aaagtcgaca ctgtcggtga ccttg                                            25

<210> SEQ ID NO 15
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 15
aaaggatcca tgttgataag aatcatctta cac                                   33

<210> SEQ ID NO 16
<211> LENGTH: 26
<212> TYPE: DNA
<213> ORGANISM: Artificial Sequence

```
<220> FEATURE:
<223> OTHER INFORMATION: Chemically Synthesized

<400> SEQUENCE: 16
aaactgcagt ggcgttgcga tgatga                                              26

<210> SEQ ID NO 17
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 17
aaactgcagc aagtttcggc tatggcg                                             27

<210> SEQ ID NO 18
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 18
aaagctgacc gcacgataac gatatgtctg                                          30

<210> SEQ ID NO 19
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 19
aaagcagtag aattcttcaa aagt                                                24

<210> SEQ ID NO 20
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 20

Lys Ala Val Glu Phe Phe Lys Ser
1               5

<210> SEQ ID NO 21
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 21
acgccactgc agcaagtt                                                       18

<210> SEQ ID NO 22
<211> LENGTH: 6
```

-continued

```
<212> TYPE: PRT
<213> ORGANISM: Artificial Sequence
<220> FEATURE:
<223> OTHER INFORMATION: Chemically Synthesized

<400> SEQUENCE: 22

Thr Pro Leu Gln Gln Val
1               5
```

PASTEURELLA MULTOCIDA STRAINS AND VACCINES HAVING HYAC AND NANP DELETIONS

REFERENCE TO RELATED APPLICATIONS

This application claims the benefit of U.S. Provisional Patent Application No. 63/085,495, filed Sep. 30, 2020. The content of this provisional patent application is hereby expressly incorporated by reference in its entirety.

FIELD OF THE INVENTION

The present invention relates generally to novel attenuated *Pasteurella multocida* bacterial strains that comprise specific genetic modifications, that are safe and efficacious as vaccines, and which provide cross protection against infection of bovines by the very wide variety of *P. multocida* strains that are relevant to worldwide bovine disease. The invention further relates to methods of producing the attenuated bacteria, and the further identification of nucleic acid variations that are associated with lessened pathogenicity. The invention further relates to live attenuated *Pasteurella multocida* having such properties, although the corresponding inactivated bacteria are also useful in the practice of the invention. The invention generally relates to methods of formulating appropriate vaccine compositions, including recombinant assembly of the appropriate bacteria, culturing thereof, and providing vaccinating compositions which may include antigen corresponding to numerous other important bovine pathogens.

SEQUENCE LISTING

The instant application contains a Sequence Listing which has been submitted via EFS-Web as ASCII compliant text file format (.txt), and is hereby incorporated by reference in its entirety. The ASCII file was created on Sep. 30, 2020, is named SequenceListing, and has 28 kilobytes. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BACKGROUND OF THE INVENTION

*Pasteurella multocida*, a Gram-negative coccobacillus of the Family Pasteurellaceae, is a common bacterial isolate recovered from pneumonic bovine lung, and it is one of the major causes of Bovine Respiratory Disease (BRD) in the United States (see D. Griffin, Bovine pasteurellosis and other bacterial infections of the respiratory tract. Vet. Clin. North Am. Food Anim. Pract., 2010. 26:57-71). *Pasteurella multocida* is frequently isolated in fatal BRD cases from feedlots and often is a component of enzootic pneumonia in dairy calves (see D. Griffin, 2010, supra). Involvement of *P. multocida* in these syndromes is well established, however both diseases are recognized as being multi-factorial in origin where infectious and non-infectious factors combine to produce these illnesses. For example, concurrent infections with other bovine bacterial and viral respiratory organisms and environmental stressors are recognized as contributors to these complex syndromes (see Yates W D. A review of infectious bovine rhinotracheitis, shipping fever pneumonia and viral-bacterial synergism in respiratory disease of cattle. *Can J Comp Med.* 1982; 46(3):225-263)

*P. multocida* is classified by capsular serogroups and somatic (LPS) serotypes, with 5 capsular (A, B, D, E, F) and 16 somatic types described, respectively (see G. Carter, Pasteurellosis: *Pasteurella multocida* and *Pasteurella hemolytica*. Adv. Vet. Sci., 1967. 11:321-792; and Heddleston, et al., Fowl cholera: gel diffusion precipitin test for serotyping *Pasteruella multocida* from avian species. Avian Dis., 1972. July-September; 16(4):925-36). There is a general specificity with disease, in that *P. multocida* capsular type A isolates are the major causes of BRD and enzootic pneumonia. *P. multocida* capsule types B and E cause hemorrhagic septicemia, a lethal disease in cattle and water buffalo (see, for example R. Verma and T. Jaiswal, Haemorrhagic septicaemia vaccines. Vaccine, 1998. 16:1184-1192). *P. multocida* is commonly carried for protracted periods in the nasopharynx and the palatine tonsil of weaned calves and feedlot cattle (see J. Allen, et al., Changes in the bacterial flora of the upper and lower respiratory tracts and broncho-alveolar lavage differential cell counts in feedlot calves treated for respiratory diseases. Can. J. Vet. Res., 1992. 56:177-183), and both reservoirs of bacteria can be sources for dissemination to the lower respiratory tract (see also D Griffin, et al., Bacterial pathogens of the bovine respiratory tract. Vet. Clin. North Am. Food Anim. Pract., 2010. 26:381-394).

Reported isolation rates in clinically normal calves are between 20% and 60%, while *P. multocida* isolation from nasal passages of clinically ill animals is even greater (see D. Griffin, D., Bovine pasteurellosis and other bacterial infections of the respiratory tract. Vet. Clin. North Am. Food Anim. Pract., 2010. 26:57-71). Frequently, *P. multocida* is observed in chronic cases of BRD, often together with other bacteria, and it is believed that prior lung damage favors establishment of *P. multocida* and disease severity.

Known virulence factors of *P. multocida* include capsule and sialic acid incorporation into LPS. See, for example, (1) K. Snipes, et al., Fate of *Pasteurella multocida* in the blood vascular system of turkeys following intravenous inoculation: comparison of an encapsulated, virulent strain with its avirulent, acapsular variant. Avian Dis., 1986. 31, 254-259; (2) J. Chung, et al., Role of capsule in the pathogenesis of fowl cholera caused by *Pasteurella multocida* serogroup A. Infect. Immun., April 2001. 69(4):2487-92; (3) T. Fuller, et al., Identification of *Pasteurella multocida* virulence genes in a septicemic mouse model using signature-tagged mutagenesis. Microb. Pathog. 2000. 29:25-38; and (4) F. Tatum, et al., Sialic acid uptake is necessary for virulence of *Pasteurella multocida* in turkeys. Microb. Pathog., 2009. 46:337-344.

The composition (structure) of *P. multocida* components that define serogroup A capsule is primarily hyaluronic acid, a polymer consisting of alternating units of D-glucuronic acid and N-acetyl-D-glucosamine. The genes required for the biosynthesis of hyaluronic acid are encoded within an operon comprised of hyaE, hyaD, hyaC, and hyaB. It has been shown that the *P. multocida* serogroup A capsule plays a significant role in resistance to complement-mediated killing (see K. Snipes et al., Fate of *Pasteurella multocida* in the blood vascular system of turkeys following intravenous inoculation: comparison of an encapsulated, virulent strain with its avirulent, acapsular variant. Avian Dis. 1986. 31, 254-259). A *P. multocida* mutant devoid of capsule type A is attenuated in avian and mouse models (see J. Chung, et al., Role of capsule in the pathogenesis of fowl cholera caused by *Pasteurella multocida* serogroup A. Infect Immun. 2001 April; 69(4):2487-92).

Sialic acid is a generic term for the N- or O-substituted derivatives of neuraminic acid, a monosaccharide possessing a nine-carbon backbone. Modification of gram-negative bacteria with sialic acid is a well-documented virulence feature (see E. Vimr et al., To sialylate, or not to sialylate: that is the question. Trends Microbiol., June 2002. 10(6): 254-7). A wide range of pathogens and commensal bacteria either synthesize sialic acid de novo or procure sialic acids from host tissues which are internalized and incorporated into LPS and capsule (see S. Steenbergen, et al., Sialic acid metabolism and systemic pasteurellosis. Infect. Immun. March 2005. 73(3):1284-94). Over 20 microbial pathogens are known to use surface sialylation as a form of molecular mimicry. Incorporation of sialic acid molecules onto the bacterial surfaces is known to impart stealth properties which enable evasion of host defense mechanisms (see H. Smith et al., Sialylation of lipopolysaccharide: a major influence on pathogenicity. Microb. Path. December 1995. 19(6):365-77).

Previously, a *P. multocida* A:3 (P1059) ΔnanP ΔnanU mutant was shown to be unable to take up sialic acid from growth media and when grown in the presence of radiolabeled sialic acid (F. Tatum, et al. Sialic acid uptake is necessary for virulence of *Pasteurella multocida* in turkeys. Microb Pathog. 2009. 46:337-344). Moreover, the mutant exhibited no radiolabeled sialic acid incorporation into cellular components, unlike the parent, indicating the mutant was unable to take up and modify cell surface molecules with exogenous sialic acid. The *P. multocida* ΔnanP ΔnanU mutant also exhibited greatly reduced virulence in turkeys compared to wild-type parent (F. Tatum, et al., 2009, supra).

U.S. Pat. No. 7,763,262 describes attenuated *Pasteurella multocida* involving mutations in the yiaO ("nanP") gene. However, it has generally become recognized that providing bacteria wherein attenuation is dependent on mutations in two or more genes may provide a more appropriate loss of virulence, and additional safety. In this regard, U. S. Patent Publication 2018/0015157 discloses attenuated *Pasteurella multocida* having deletions in both hyaD and nanPU.

Thus, there is potential to develop further modified *Pasteurella multocida* organisms as effective vaccines, including in combination with antigens provided from other pathogens.

SUMMARY OF THE INVENTION

The present invention provides an isolated and attenuated live *Pasteurella multocida* (*P. multocida*) bacterium that is defective for biosynthesis of hyaluronic acid resulting from a mutation in the hyaC gene, and defective for surface sialylation resulting from a mutation in the nanP gene, which are useful as vaccines. The attenuating mutations are selected from the group consisting of deletion of the entire gene, partial deletions, frameshift mutations, nucleotide insertions, and nucleotide replacements resulting in replacement codons. The resultant proteins expressed from the hyaC gene or the nanP gene are inactive, or at least substantially so, causing the organism to be substantially reduced in virulence. Generally, it is preferred that the attenuated bacterium is provided from Serogroup A, but the resultant bacteria, as attenuated live vaccines also provide protection against A, B, D, E, F-type capsular organisms.

In an embodiment, the *Pasteurella multocida* bacterium contains, prior to modification, a wild type hyaC DNA sequence that encodes an amino acid sequence of SEQ ID NO:9, or any amino acid sequence that is at least 80% identical thereto; and contains, prior to modification, a wild type nanP DNA sequence that encodes an amino acid sequence of SEQ ID NO:2, or any amino acid sequence that is at least 80% identical thereto. In a resultant embodiment, the attenuated bacterium comprises a nanP gene sequence that encodes an amino acid sequence of SEQ ID NO:4 and a hyaC gene sequence that encodes an amino acid sequence of SEQ ID NO:11.

In a highly preferred embodiment, the mutation in the hyaC gene and/or the mutation in the nanP gene is fully inactivating.

Figure 1:
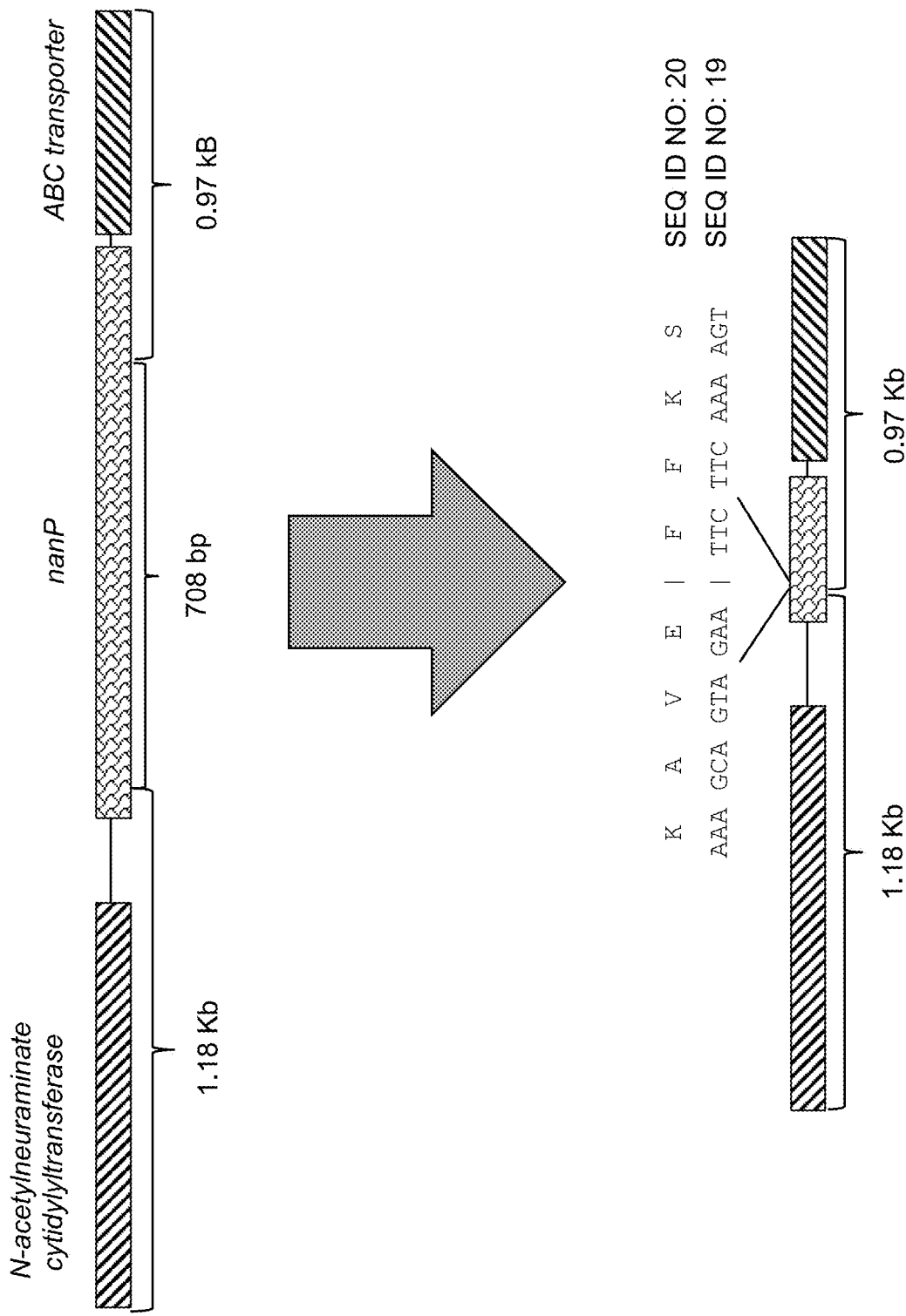
FIG. 1 shows the general construction of the ΔnanP mutation in *P. multocida*.

BRIEF DESCRIPTION OF THE
POLYNUCLEOTIDE AND POLYPEPTIDE
SEQUENCES

The various polynucleotide and polypeptides involved with this invention, as well as the sequence identifier assigned to each are listed below in Table A.

TABLE A

POLYNUCLEOTIDES AND POLYPEPTIDES

| Identifier | Matter |
| --- | --- |
| SEQ ID NO: 1 | Wild type (unmodified) nanP nucleotide sequence |
| SEQ ID NO: 2 | Wild type (unmodified) nanP amino acid sequence |
| SEQ ID NO: 3 | ΔnanP nucleotide sequence |
| SEQ ID NO: 4 | ΔnanP amino acid sequence |
| SEQ ID NO: 5 | Polynucleotide contained in fragment amplified by primers of SEQ ID NO: 13 and SEQ ID NO: 14 |
| SEQ ID NO: 6 | Nucleotide sequence of ΔhyaC with surrounding operons |
| SEQ ID NO: 7 | Nucleotide sequence of ΔnanP with surrounding operons |
| SEQ ID NO: 8 | Wild type (unmodified) hyaC nucleotide sequence |
| SEQ ID NO: 9 | Wild type (unmodified) hyaC amino acid sequence |
| SEQ ID NO: 10 | Nucleotide sequence of wild-type hyaC and surrounding operons |
| SEQ ID NO: 11 | ΔhyaC amino acid sequence |
| SEQ ID NO: 12 | ΔhyaC nucleotide sequence |
| SEQ ID NO: 13 | Primer 1062 Bam-nanP-F nucleotide sequence |
| SEQ ID NO: 14 | Primer 1062 Sal-nanP-R nucleotide sequence |
| SEQ ID NO: 15 | Primer 1062 Bam-hyaC-F nucleotide sequence |
| SEQ ID NO: 16 | Primer 1062 Pst-hyaC-R nucleotide sequence |
| SEQ ID NO: 17 | Primer 1062 Pst-hyaC-F nucleotide sequence |
| SEQ ID NO: 18 | Primer 1062 Sal-hyaC-R nucleotide sequence |
| SEQ ID NO: 19 | Nucleotide sequence surrounding ΔnanP deletion site |
| SEQ ID NO: 20 | Amino acid sequence surrounding ΔnanP deletion site |

TABLE A-continued

POLYNUCLEOTIDES AND POLYPEPTIDES

| Identifier | Matter |
|---|---|
| SEQ ID NO: 21 | Nucleotide sequence surrounding ΔhyaC deletion site |
| SEQ ID NO: 22 | Amino acid sequence surrounding ΔhyaC deletion site |

DETAILED DESCRIPTION OF THE INVENTION

Definitions

Unless otherwise defined herein, scientific and technical terms used in connection with the present embodiments shall have the meanings that are commonly understood by those of ordinary skill in the art. Further, unless otherwise required by context, singular terms shall include pluralities, and plural terms shall include the singular.

The term "adjuvant", as used herein, means a pharmacological or immunological agent that modifies the effect of other agents, such as a drug or immunogenic composition. Adjuvants are often included in immunogenic compositions to enhance the recipient's immune response to a supplied antigen. See below for a further description of adjuvants.

The terms "antibody" or "antibodies", as used herein, mean an immunoglobulin molecule able to bind to an antigen by means of recognition of an epitope. Immunoglobulins are serum proteins composed of "light" and "heavy" polypeptide chains, which have "constant" and "variable" regions, and are divided into classes (e.g., IgA, IgD, IgE, IgG, and IgM) based on the composition of the constant regions. An antibody that is "specific" for a given antigen indicates that the variable regions of the antibody recognize and bind a particular antigen exclusively. Antibodies can be a polyclonal mixture, or monoclonal. They can be intact immunoglobulins derived from natural or recombinant sources or can be immunoreactive portions of intact immunoglobulins. Antibodies can exist in a variety of forms, including Fv, Fab', F(ab')2, Fc, as well as single chain. An antibody can be converted to an antigen-binding protein, which includes, but is not limited to, antibody fragments. As used herein, the term "antigen binding protein", "antibody" and the like, which may be used interchangeably, refer to a polypeptide or polypeptides, or fragment(s) thereof, comprising an antigen binding site. The term "antigen binding protein" or "antibody" preferably refers to monoclonal antibodies and fragments thereof, and immunologic-binding equivalents thereof that can bind to a particular protein and fragments thereof. As used herein, the term encompasses not only intact polyclonal or monoclonal antibodies, but also fragments thereof. For the purposes of the present invention, "antibody" and "antigen binding protein" also includes antibody fragments, unless otherwise stated. Exemplary antibody fragments include Fab, Fab', F(ab')2, Fv, scFv, Fd, dAb, diabodies, their antigen-recognizing fragments, small modular immunopharmaceuticals (SMIPs) nanobodies and the like, all recognized by one of skill in the art to be an antigen binding protein or antibody fragment, and any of above-mentioned fragments and their chemically or genetically manipulated counterparts, as well as other antibody fragments and mutants thereof, fusion proteins comprising an antibody portion, and any other modified configuration of the immunoglobulin molecule that comprises an antigen recognition site. Antibodies and antigen binding proteins can be made, for example, via traditional hybridoma techniques (Kohler et al., Nature 256:495 499 (1975)), recombinant DNA methods (U.S. Pat. No. 4,816,567), or phage display techniques using antibody libraries (Clackson et al., Nature 352:624 628 (1991); Marks et al., J. Mol. Biol. 222:581 597 (1991)). For various other antibody production techniques, see Antibodies: A Laboratory Manual, eds. Harlow et al., Cold Spring Harbor Laboratory, 1988 as well as other techniques that are well known to those skilled in the art.

"Antigen", as used herein, means a molecule that contains one or more epitopes (linear, conformational or both), that upon exposure to a subject, will induce an immune response that is specific for that antigen. An epitope is the specific site of the antigen which binds to a T-cell receptor or specific B-cell antibody, and typically comprises about 3 to about 20 amino acid residues. The term "antigen" can also refer to subunit antigens-antigens separate and discrete from a whole organism with which the antigen is associated in nature—as well as killed, attenuated, or inactivated bacteria, viruses, fungi, parasites, or other microbes. The term "antigen" also refers to antibodies, such as anti-idiotype antibodies or fragments thereof, and to synthetic peptide mimotopes that can mimic an antigen or antigenic determinant (epitope). The term "antigen" also refers to an oligonucleotide or polynucleotide that expresses an antigen or antigenic determinant in vivo, such as in DNA immunization applications. An "antigen", as used herein, is a molecule or a portion of a molecule capable of being specifically bound by an antibody or antigen binding protein. In particular, an antibody, or antigen binding protein, will bind to epitopes of the antigen. An epitope, as used herein, refers to the antigenic determinant recognized by the hypervariable region, or Complementarity Determining Region (CDR), of the variable region of an antibody or antigen binding protein.

The term "animal", as used herein, means any animal that is susceptible to infection by *Mycoplasma bovis*, both domesticated and wild. Preferably, "animal", as used herein, refers to a bovine.

The term "attenuated", as used herein, refers to a strain of a microorganism whose pathogenicity has been reduced so that it will generally initiate an immune response but without producing disease. An attenuated strain is less virulent than the parental strain from which it was derived. Attenuated microorganisms can be screened in vitro or in vivo to confirm that they are less pathogenic than its parental strain. Conventional means are used to introduce attenuating mutations, such as in vitro passaging, as well as chemical mutagenesis. An alternative means of attenuating comprises making pre-determined mutations using site-directed mutagenesis, where one or more mutations may be introduced. The term "more attenuated", as used herein, refers to a strain which has been further modified beyond the attenuated strain from which it was derived. This further attenuation can be achieved through additional in vitro passaging, or additional rounds of chemical or site-directed mutagenesis. To be useful as a live vaccine, any attenuated organism must nonetheless cause the host immune system to initiate an effective immune response, which may require some growth of the organism.

The terms "bacteria", "bacterial species", "bacterium", and the like, as used herein, mean a large domain of prokaryotic microorganisms.

The term "bovine", as used herein, means a diverse group of medium- to large-sized ungulates, generally having cloven hoofs, and at least one of the sexes having true horns. Bovines include, but are not limited to, domestic cattle, bison, African buffalo, water buffalo, yak, and four-horned or spiral-horned antelope.

The term "chemical mutagenesis", as used herein, means the use of a compound that increases the frequency of some types of mutation(s) occurring above the natural background level. The compounds used can vary in their potency, since they can differ in their ability to enter a cell, in the extent of their reactivity with nucleic acids, in their general toxicity, and in the likelihood that the type of chemical change they introduce into the nucleic acid will be corrected by a endogenous repair system.

The term "immunogenic composition" or "immunizing amount", as used herein, means a composition that generates an effective immune response (i.e., has effective and/or at least partially protecting immunogenic activity) when administered alone, or with a pharmaceutically-acceptable carrier, to an animal. The immune response can be a cellular immune response mediated primarily by cytotoxic T-cells, or a humoral immune response mediated primarily by helper T-cells, which in turn activate B-cells, leading to antibody production. In addition, specific T-lymphocytes or antibodies can be generated to allow for the future protection of an immunized host.

The term "isolated", as used herein, means that the referenced material is removed from some of the components of the environment in which it is normally found. Thus, an isolated biological material can be free of some cellular components, i.e., components of the cells in which the material is found or produced. In the case of nucleic acid molecules, an isolated nucleic acid includes, for example, a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes located upstream or downstream of the nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified. An "isolated" or "purified" polypeptide or polynucleotide, e.g., an "isolated polypeptide," or an "isolated polynucleotide", is purified to a state beyond that in which it exists in nature. For example, the "isolated" or "purified" polypeptide or polynucleotide, can be substantially free of cellular material or other contaminating proteins from the cell or tissue source from which the protein or polynucleotide is derived, or substantially free from chemical precursors or other chemicals when chemically synthesized. The preparation of antigen binding protein having less than about 50% of non-antigen binding protein (also referred to herein as a "contaminating protein"), or of chemical precursors, is considered to be "substantially free." 40%, 30%, 20%, 10% and more preferably 5% (by dry weight), of non-antigen binding protein, or of chemical precursors, is considered to be substantially free.

The term "medicament", as used herein, means an agent that promotes recovery from an infection, injury or ailment; a medicine.

The term "mutant", as used herein, means an individual or organism arising or resulting from an instance of mutation, which is a base-pair sequence change within the nucleic acid or chromosome of an organism, and results in the creation of a new character or trait not found in the wild-type individual or organism.

The term "parent" or "parental strain", as used herein, means the entity from which offspring, or progeny, are derived. The term "progeny", as used herein, means that produced by, or derived from, one or more parents or parental strains.

The terms "prevent", "preventing" or "prevention", and the like, as used herein, mean to inhibit the replication of a microorganism, to inhibit transmission of a microorganism, or to inhibit a microorganism from establishing itself in its host. These terms, and the like, can also mean to inhibit or block one or more signs or symptoms of infection.

The terms "reverse engineer" or "reverse mutagenize", as used herein, mean to reintroduce by genetic means (e.g. polymerase chain reaction, or PCR) the original nucleotide sequence occurring at a particular position(s) within a microorganism's genome, wherein that sequence had previously been changed.

The terms "serial passage" or "serial passaging", as used herein, mean a method for purifying an organism, preferably a microorganism, to obtain a clonally pure population. The terms can also refer to a technique for attenuating, or weakening, the virulence of an organism, preferably a microorganism.

The term "therapeutically effective amount" (or "effective amount"), as used herein, means an amount of an active ingredient, e.g., an agent according to the invention, with or without an adjuvant, as appropriate under the circumstances, provided in a single or multiple doses as appropriate, sufficient to effect beneficial or desired results when administered to a subject or patient. An effective amount can be administered in one or more administrations, applications or dosages. A therapeutically effective amount of a composition according to the invention may be readily determined by one of ordinary skill in the art, and provides a measurable benefit to a patient, such as protecting the animal from subsequent challenge with a similar pathogen.

As used herein, the terms "therapeutic" or "treatment" encompass the full spectrum of treatments for a disease or disorder. By way of example, a "therapeutic" agent of the invention may act in a manner, or a treatment may result in an effect, that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

The term "veterinarily-acceptable carrier", as used herein, refers to substances which are, within the scope of sound medical judgment, suitable for use in contact with the tissues of animals, without undue toxicity, irritation, allergic response, and the like, commensurate with a reasonable benefit-to-risk ratio, and effective for their intended use.

Partial Deletions of the *Pasteurella multocida* hyaC and nanP Genes

Examples 1-3 below present the construction of particular double deletion constructs involving hyaC and nanP. Those skilled in the art will realize that any other deletion within the coding regions of these genes that is of generally sufficient length, or which involves particular amino acids involved in specific structural or function roles for the encoded proteins, should provide equally useful examples of the invention. Thus, it is by no means necessary to delete the entire open reading frame, rather, reference to standard methods of bioinformatics analysis will suggest numerous other equivalent and effective mutations of hyaC and nanP. Thus, starting with the wild-type hyaC DNA sequence (SEQ ID NO: 8) and the equivalent amino acid sequence (SEQ ID NO: 9), numerous appropriate deletion fragments can be identified. Similarly, useful in this regard is the unmodified nanP DNA sequence (SEQ ID NO: 1) and the corresponding amino acid sequence (SEQ ID NO: 2). Additionally, it is possible to provide even full length copies of the nanP and hyaC genes, in which particular amino acid codons are changed, so that although a full length encoding sequence is provided, in fact, owing to one or more key amino acid mutations, the resultant protein is non-functional, and the organism is attenuated. Thus, the scope of mutations that can be made to attain nanP/hyaC attenuation is quite wide, and the construction techniques are quite varied, once the practitioner realizes the overall value of such mutations.

In the instant examples, ΔnanP was created by removing 708 nucleotides from the wildtype nanP open reading frame. Representative examples of partial truncation of nanP that may be equally effective in achieving *P. multocida* attenuation include removing additional nucleotides, or removing less nucleotides, i.e., removing any number of nucleotides from 1 to 984 from the nanP gene to achieve *P. multocida* attenuation. In the instant examples, ΔhyaC was created by removing 500 nucleotides from the wildtype hyaC open reading frame. Representative examples of truncations of hyaC that may be equally effective in achieving *P. multocida* attenuation include removing additional nucleotides, or removing less nucleotides, i.e., removing any number of nucleotides from 1 to 1,107 nucleotides from the hyaC gene to achieve *P. multocida* attenuation.

Point mutations may also be introduced into the nanP and/or hyaC open reading frames to achieve *P. multocida* attenuation. Examples of the types of point mutations that may be introduced are well known to those skilled in the art.

Besides mutations in hyaC, nanP genes, optionally other genes may be mutated in a *Pasteurella multocida* (*P. multocida*) bacterium of serogroup A to obtain an attenuated bacterium. The optionally mutated genes may be one or more of Fis, or Leukotoxin A virulence genes.

In regard of such equivalent examples of the present invention and referring to the construction and assembly of any such final genomic sequences, the following overall definitions and technical standards apply.

For purposes of the present invention, the nucleotide sequence of a second polynucleotide molecule (either RNA or DNA) is "homologous" to the nucleotide sequence of a first polynucleotide molecule, or has "identity" to said first polynucleotide molecule, where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. Homologous polynucleotide sequences also refers to sense and anti-sense strands, and in all cases to the complement of any such strands Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Maryland, USA) of the United States National Institute of Health). In a specific example for calculations according to the practice of the present invention, reference is made to BLASTP 2.2.6 [Tatusova T A and T L Madden, "BLAST 2 sequences—a new tool for comparing protein and nucleotide sequences." (1999) FEMS Microbiol Lett. 174:247-250.]. Briefly, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 89:10915 10919. 1992). The percent identity is then calculated as: Total number of identical matches×100/divided by the length of the longer sequence+number of gaps introduced into the longer sequence to align the two sequences.

Preferably, a homologous nucleotide sequence has at least about 75% nucleotide sequence identity, even more preferably at least about 80%, 85%, 90% 95%, 96%, 97%, 98% and 99% nucleotide sequence identity. Since the genetic code is degenerate, a homologous nucleotide sequence can include any number of "silent" base changes, i.e. nucleotide substitutions that nonetheless encode the same amino acid.

A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tyrptophan and phenylalanine. Amino acids can be classified according to physical properties and contribution to secondary and tertiary protein structure. A conservative substitution is recognized in the art as a substitution of one amino acid for another amino acid that has similar properties. Exemplary conservative substitutions may be found in WO 97/09433, page 10, published Mar. 13, 1997 (PCT/GB96/02197, filed Sep. 6, 1996. Alternatively, conservative amino acids can be grouped as described in Lehninger, (Biochemistry, Second Edition; Worth Publishers, Inc. NY:NY (1975), pp. 71-77). Additional suitable conservative changes and the application thereof are described below.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 (or any other particular polynucleotide sequence) if it hybridizes to the complement of SEQ ID NO:1 under moderately stringent conditions, e.g., hybridization to filter-bound DNA in 0.5 M NaHPO4, 7% sodium dodecyl sulfate (SDS), 1 mM EDTA at 65° C., and washing in 0.2×SSC/0.1% SDS at 42° C. (see Ausubel et al editors, Protocols in Molecular Biology, Wiley and Sons, 1994, pp. 6.0.3 to 6.4.10), or conditions which will otherwise result in hybridization of sequences that encode a PRRS virus as defined below. Modifications in hybridization conditions can be empirically determined or precisely calculated based on the length and percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, New York (1989), pp. 9.47 to 9.51.

In another embodiment, a second nucleotide sequence is homologous to SEQ ID NO:1 (or SEQ ID NO:8, or any other sequence of the invention) if it hybridizes to the complement of SEQ ID NO:1 (or other appropriate sequence) under highly stringent conditions, e.g. hybridization to filter-bound DNA in 0.5 M NaHPO4, 7% SDS, 1 mM EDTA at 65° C., and washing in 0.1×SSC/0.1% SDS at 68° C., as is known in the art (Ausebel et al. Current Protocols in Molecular Biology, Greene Publishing and Wiley Interscience, New York, 1989.

It is furthermore to be understood that the isolated polynucleotide molecules and the isolated RNA molecules of the present invention include both synthetic molecules and molecules obtained through recombinant techniques, such as by in vitro cloning and transcription.

Polynucleotide molecules can be genetically mutated using recombinant techniques known to those of ordinary skill in the art, including by site-directed mutagenesis, or by random mutagenesis such as by exposure to chemical mutagens or to radiation, as known in the art." The mutations may be carried out by standard methods known in the art, e.g. site directed mutagenesis (see e.g. Sambrook et al. (1989) Molecular Cloning: A Laboratory Manual, 2nd Ed., Cold Spring Harbor Laboratory Press, Cold Spring Harbor, N.Y.) of an infectious copy as described (e.g. Meulenberg et al., Adv. Exp. Med. Biol., 1998, 440:199-206).

Vaccine Compositions of the Invention

The present invention identifies genes, and gene sequences that are involved in the attenuation of *Pasteurella multocida* and are useful in the recombinant construction of attenuated bacteria and that are highly useful as bovine vaccines. Guidance derived from these discoveries also permits the screening and isolation of natural strains, or strains produced by routing culturing, that may evidence similar properties. Such attenuated bacteria are particularly useful for the preparation as live vaccines, which may further contain antigenic components (live whole bacteria, bacterins, antigenic individual proteins or other macromolecules, and live and inactivated viruses) in order to provide combination vaccines. In this regard, the those skilled in the art will appreciate that any such combination formulations may involve multiple bottle presentations, with final dilutions, combination, and mixing, as the conditions of optimal storage, or combination with adjuvants, may result in incompatibilities, for example, an adjuvant useful in regard of a skilled bacterial component may be incompatible for long term storage of a contained live viral or bacterial component.

The *Pasteurella multocida* bacterium contains, prior to modification, a wild type hyaC DNA sequence that is SEQ ID NO:8 or any DNA sequence that is at least 80% identical thereto; and contains, prior to modification, a wild type nanP DNA sequence that is SEQ ID NO:1 or any DNA sequence that is at least 80% identical thereto. In a resultant preferred embodiment, the attenuated bacterium comprises a nanP gene sequence that encodes a polypeptide of SEQ ID NO: 4, and a hyaC gene sequence that encodes a polypeptide of SEQ ID NO: 11.

Resultant attenuated *P. multocida* of the invention elicit strong immune responses in bovines which are protective against disease. As noted above, *P. multocida* is classified by capsular serogroups and somatic (LPS) serotypes, with 5 capsular (A, B, D, E, F) and 16 somatic types described, respectively (see G. Carter, Pasteurellosis: *Pasteurella multocida* and *Pasteurella hemolytica*. Adv. Vet. Sci., 1967. 11:321-792. Although the attenuated strains of the invention provide protection against disease caused by a wide variety of *P. multocida* serogroups, and protection against capsular serotype A is preferred.

Two Component Composition

An additional bacterial pathogen of major significance in cattle is *Pasteurella* (*Mannheimia*) *haemolytica*. Although many pathogens are known to contribute to bovine respiratory disease complex (BRDC), *M. haeomolytica* is recognized as a major contributor to severe forms of "shipping fever in feedlot cattle, and pneumonia in calves, including on dairy farms. In fact, by contributing to acute fibrinous lobar pleuropneoumina, this pathogen may actually be the dominant pathogen associated with death under such disease conditions. One example of a highly effective *M. haemolytica* vaccine is One Shot®, manufactured by Zoetis, USA, which provides excellent protection against *M. haemolytica* Type A-1 infection, and which comprises a therapeutically effective amount of Type A-1 leukotoxoid, capsular antigen, soluble antigens, and inactivated cells, which is capable of providing protection in bovines in one dose only. In such preferred example, the antigenic components are provided from strain ATCC No. 55318, see also U.S. Pat. No. 5,855,894.

Thus, in a preferred embodiment of the present invention, there is provided a freeze dried preparation of *M. haemolytica* antigen (as described above) and *P. multocida* live attenuated bacteria, which is reconstituted immediately prior to vaccine use, with a diluent component that comprises one or more adjuvants, such as aluminum hydroxide gel and mineral oil/lecithin emulsion. One such preferred adjuvant composition is a 5% v/v mineral oil/lecithin emulsion adjuvant "Amphigen"® provided with 12% v/v aluminum hydroxide gel and saline as adjuvant/diluent (see below in regard of adjuvant formulations). Such vaccines may be administered in one dose, two dose, or multiple dose presentations as needed, and the Examples below provide guidance on dosing amounts and timing thereof, dependent on the actual antigenic compositions being used.

Those skilled in the art will recognize that there are many two dose compositions (i.e. providing protection against two pathogens) that are immediately available according to the practice of the invention. Such compositions can be provided from one, two, or three separate vials, with mixing immediately prior to use in an animal, dependent on the stability requirements of the involved components. Thus, in a most typical embodiment, where bacterin membrane components might be damaged by an adjuvant (further depending on which adjuvant is selected), or live bacterial and live virus antigenic component might deteriorate, the antigenic components can be provided from a first source (such as a lyophilized cake), wherein an adjuvant is provided from a diluent bottle, mixed immediately prior to vaccination. In this regard suitable additional live or killed viral and bacterial components include those provided from Bovine Diarrhea Virus (BVDV), Bovine Rhinotracheitis Virus (IBR), Parainfluenza 3 Virus (PI3), and Bovine Respiratory Syncytial Virus (BRSV), Bovine Corona Virus (BCV, *Mycoplasma bovis, Histophilus somni* (somnus) and Clostridials [*Perfringens* Types A, B, C, D, *Tetani, Speticum, Sordellii, Haemolyticum, Novyi, Chauvoi*]

Multiple Component Compositions A preferred multicomponent vaccine includes the use of the attenuated *P. multocida* component in combination with Bovishield Gold® of Zoetis which also provides Bovine Diarrhea Virus (BVDV), Bovine Rhinotracheitis Virus (IBR), Parainfluenza 3 Virus (PI3), and Bovine Respiratory Syncytial Virus (BRSV), for which the specific viral isolates are as follows. Bovine Rhinotracheitis Virus (IBR) Passage C-13 obtained from Cutter Labs in 1965, passaged on bovine kidney cells (NL-BK-1A), approved by APHIS as production Master Seed in 1971; Parainfluenza3 Virus (PI3) "Reisinger" isolate at University of Nebraska in 1969, passaged on bovine kidney cells (NL-BK-1A), approved by APHIS as production Master Seed in 1971; Bovine Respiratory Syncytial Virus (BRSV) Isolate from Iowa outbreak, designated "BRSV/375" by VMRD, Ames, IA, and subsequently passaged at Norden Labs in NL-BK and BT cells, and approved by APHIS as production Master Seed in 1982; Bovine Virus Diarrhea Virus (BVDV) Types 1A, obtained from Whitehall in 1993 and reinnoculated into NL-BK-6 cells at Norden Labs, redesignated strain NADL MSVX+1, and approved by APHIS as production Master Seed in 1994; and Bovine Virus Diarrhea Virus (BVDV) Type 2, obtained as strain 53637 from U. of Guelph, plaque purified in NL-BT-2 cells, transferred to NL-BK-6 cells, further attenuated, and approved by APHIS as production Master Seed in 2002.

This preparation may further include inactivated *Mannheimia hemolytica*, as aforementioned thus incorporating the commercial product Bovishield Gold-One Shot®, Zoetis.

A further formulation involves Bovishield GOLD FP5 VL5 HB®, Zoetis, again provided as 2 vials for use together. First, a freeze-dried preparation of the following five non-adjuvanted Modified Live viruses: Bovine Rhinotracheitis Virus (IBR)+Parainfluenza3 Virus (PI3)+Bovine Respiratory Syncytial Virus (BRSV)+Bovine Virus Diarrhea Virus (BVDV) (both Types 1A and 2); to be mixed (at time of final product use) with another vial containing aqueous, adjuvanted combination of six (6) different killed whole bacterial pathogens comprising five (5) Leptospira1 interrogans serovars and one (1) *Campylobacter fetus*. The adjuvant provided in the bacterial component confers "fetal protection" against IBR and BVDV viruses, see below. The antigenic components thereof are for viruses: Bovine Rhinotracheitis Virus (IBR) Passage C-13 obtained from Cutter Labs in 1965, passaged on bovine kidney cells (NL-BK-1A), approved by APHIS as production Master Seed in 1971; Parainfluenza3 Virus (PI3) "Reisinger" isolate at University of Nebraska in 1969, passaged on bovine kidney cells (NL-BK-1A), approved by APHIS as production Master Seed in 1971; Bovine Respiratory Syncytial Virus (BRSV) Isolate from Iowa outbreak, designated "BRSV/375" by VMRD, Ames, IA, and subsequently passaged at Norden Labs in NL-BK and BT cells, and approved by APHIS as production Master Seed in 1982; Bovine Virus Diarrhea Virus (BVDV) Types 1A, obtained from Whitehall in 1993 and re-inoculated into NL-BK-6 cells at Norden Labs, redesignated strain NADL MSVX+1, and approved by APHIS as production Master Seed in 1994; and Bovine Virus Diarrhea Virus (BVDV) Type 2, obtained as strain 53637 from U. of Guelph, plaque purified in NL-BT-2 cells, transferred to NL-BK-6 cells, further attenuated, and approved by APHIS as production Master Seed in 2002. Bacteria: *L. interrogans* s. *canicola*, frozen master seed lot 10003 established July 1974 and labeled Norden L-15, APHIS approved prior to 1984; *L. interrogans* s. *grippotyphosa*, frozen master seed lot 10005 (Lepto grippo 1550) established July 1974 and APHIS approved prior to 1984; *L. borgpetersenii* s. *hardjo*, frozen master seed lot H.MP11 (from Bairnsdale Regional Veterinary Laboratory, Australia) in 1999, approval letter granted by APHIS in 2001 to Biocor (a CSL Company); *L. interrogans* s. *icterohaemorrhagiae*, frozen master seed lot 10010 established October 1975 and labeled Lepto ictero NADL, and APHIS approved prior to 1984; and *L. interrogans* s. *pomona*, frozen master seed lot 10002 established July 1974 and labeled *L. Pomona* T262 and APHIS approved prior to 1984; *Campylobacter fetus*, subspecies fetus, isolated from cattle in 1965 and designated strain 14858, redesignated strain 17761 and approved by CVB in 1981 under license from Dellen Laboratories.

Adjuvants and Excipients, Generally

In the present invention, the vaccine and/or immunogenic composition comprise an adjuvant. As used herein, "adjuvant" refers to an agent which, while not having any specific antigenic effect in itself, may stimulate the immune system, increasing the response to an antigen.

The concentration of adjuvant employed in the compositions described herein will depend upon the nature of the adjuvant. Adjuvants are typically present in the compositions described herein at a final concentration of about 1-50% (v/v) and more typically at a final concentration of about 10%, 15%, 20%, 25%, or 30% (v/v). In compositions comprising SP-Oil, for example, the adjuvant is typically present at between about 1% and about 25% (v/v), more typically between about 5% and about 15% (v/v) such as, for example, at about 10% (v/v). In compositions comprising an acrylic acid polymer and a mixture of a metabolizable oil that comprises one or more terpene hydrocarbon(s) and a polyoxyethylene-polypropylene block copolymer, for example, the ratio of acrylic acid polymer to metabolizable oil/polyoxyethylene-polypropylene block copolymer mixture is typically in a ratio of between about 1:25 and about 1:50 and typically at a final concentration of between about 1% and about 25% (v/v).

In one embodiment, the biologically acceptable adjuvant comprises SP-Oil. SP-Oil is a fluidized oil emulsion which includes a polyoxyethylene-polyoxypropylene block copolymer (Pluronic® L121, BASF Corporation), squalane, polyoxyethylene sorbitan monooleate (Tween® 80, ICI Americas), and a buffered salt solution. SP-Oil is an effective vaccine adjuvant and is able to induce both a cell-mediated (CMI) and humoral immune response when administered to a subject (see e.g. U.S. Pat. No. 5,709,860).

Polyoxyethylene-polyoxypropylene block copolymers are surfactants that aid in suspending solid and liquid components. These surfactants are commercially available as polymers under the trade name Pluronic®. The preferred surfactant is poloxamer 401 which is commercially available under the trade name Pluronic® L121. In general, the SP-Oil emulsion is an immunostimulating adjuvant mixture which will comprise about 1 to 3% vol/vol of block copolymer, about 2 to 6% vol/vol of squalane, more particularly about 3 to 6% of squalane, and about 0.1 to 0.5% vol/vol of polyoxyethylene sorbitan monooleate, with the remainder being a buffered salt solution.

In one embodiment, the SP-Oil is present at a concentration of between about 1% and about 25% v/v. In one embodiment, the SP-Oil is present at a concentration of between about 5% and about 15% v/v. In one embodiment, the SP-Oil is present at a concentration of about 10% v/v.

In additional effective embodiments the adjuvant may comprise a saponin such as Quil A, a sterol such as cholesterol, a quaternary ammonium compound such as dimethyl dioctadecyl ammonium bromide (DDA), a polymer such as polyacrylic acid (Carbopol®, Lubrizol Corporation), a glycolipid such as N-(2-Deoxy-2-L-leucylamino-b-D-glucopyranosyl)-N-octadecyldodecanoylamide hydroacetate, and an immunostimulatory oligonucleotide, including DNA-based and RNA-based oligonucleotides.

In some embodiments, the saponin for use in the present invention is Quil A and/or its derivatives. Quil A is a saponin preparation isolated from the South American tree *Quillaja saponaria* Molina, and was first described as having adjuvant activity by Dalsgaard (1974), Saponin adjuvants, Archiv. für die gesamte Virusforschung, Vol. 44, Springer Verlag, pp. 243-254. Purified fragments of Quil A have been isolated by HPLC which retain adjuvant activity without the toxicity associated with Quil A (EP 0362278), for example QS7 and QS21 (also known as QA7 and QA21). QS21 is a natural saponin derived from the bark of *Quillaja saponaria* Molina which induces CD8+ cytotoxic T cells (CTL), Th1 cells and a predominant IgG2a antibody response, and is a saponin for use in the context of the present invention. Other suitable saponins for use in the adjuvant include, but are not limited to, the QH-A, QH-B and QH-C subfractions of Quil A, those from species other than *Quillaia saponaria*, such as those from the genera *Panax* (*ginseng*), *Astragalus, Achyranthes*, Soybean, *Acacia*, and *Codonopsis*. In some embodiments, the saponin is isolated from a species other than *Quillaja saponaria*.

In some embodiments the adjuvant may comprise a sterol. Sterols share a common chemical core, which is a steroid ring structure[s] having a hydroxyl (OH) group usually attached to carbon-3. The hydrocarbon chain of the fatty-acid substituent varies in length, usually from 16 to 20 carbon atoms, and can be saturated or unsaturated. Sterols commonly contain one or more double bonds in the ring structure, and also a variety of substituents attached to the rings. Sterols and their fatty-acid esters are essentially water-insoluble. In view of these chemical similarities, it is thus likely that the sterols sharing this chemical core would have similar properties when used in the vaccine compositions of the instant invention. Sterols suitable for use in the adjuvant include cholesterol, ☐-sitosterol, stigmasterol, ergosterol, and ergocalciferol. These sterols are well known in the art, and can be purchased commercially. For example, cholesterol is disclosed in the Merck Index, 12th Ed., p. 369. The amount of sterols suitable for use in the adjuvant depends upon the nature of the sterol used. However, they are generally used in an amount of about 1 microgram to about 5,000 micrograms per dose. They also are used in an amount of about 1 microgram to about 4,000 micrograms per dose, about 1 microgram to about 3,000 micrograms per dose, about 1 microgram to about 2,000 micrograms per dose, and about 1 microgram to about 1,000 micrograms per dose. They are also used in an amount of about 5 micrograms to about 750 micrograms per dose, about 5 micrograms to about 500 micrograms per dose, about 5 micrograms to about 200 microgram per dose, about 5 microgram to about 100 micrograms per dose, about 15 micrograms to about 100 micrograms per dose, and about 30 micrograms to about 75 micrograms per dose.

In some embodiments the adjuvant may comprise a quaternary amine compound. These compounds are ammonium-based, with four hydrocarbon groups. In practice, the hydrocarbon groups are generally limited to alkyl or aryl groups. In an embodiment, the quaternary amine compound is composed of four alkyl chains, two of which are C10-C20 alkyls, and the remaining two are C1-C4 alkyls. In one embodiment, the quaternary amine is dimethyldioctadecylammonium bromide (DDA), chloride or pharmaceutically acceptable counterion.

In some embodiments the adjuvant may comprise one or more immunomodulatory agents, such as interleukins, interferons, or other cytokines. These materials can be purchased commercially. The amount of an immunomodulator suitable for use in the adjuvant depends upon the nature of the immunomodulator used and the subject. However, they are generally used in an amount of about 1 microgram to about 5,000 micrograms per dose. They also are used in an amount of about 1 microgram to about 4,000 micrograms per dose, about 1 microgram to about 3,000 micrograms per dose, about 1 microgram to about 2,000 micrograms per dose, and about 1 microgram to about 1,000 micrograms per dose.

In some embodiments the adjuvant may comprise one or more polymers such as, for example, DEAE Dextran, polyethylene glycol, and polyacrylic acid and polymethacrylic acid (eg, CARBOPOL®). Such material can be purchased commercially. The amount of polymers suitable for use in the adjuvant depends upon the nature of the polymers used. However, they are generally used in an amount of about 0.0001% volume to volume (v/v) to about 75% v/v. In other embodiments, they are used in an amount of about 0.001% v/v to about 50% v/v, of about 0.005% v/v to about 25% v/v, of about 0.01% v/v to about 10% v/v, of about 0.05% v/v to about 2% v/v, and of about 0.1% v/v to about 0.75% v/v. In another embodiment, they are used in an amount of about 0.02% v/v to about 0.4% v/v. DEAE-dextran can have a molecular size in the range of 50,000 Da to 5,000,000 Da, or it can be in the range of 500,000 Da to 2,000,000 Da. Such material may be purchased commercially or prepared from dextran.

In some embodiments the adjuvant may comprise a glycolipid. Suitable glycolipids are generally those which activate a Th2 response. The glycolipids include, without limitations, those encompassed by Formula I, and that are generally described in US Publication 20070196384 (Ramasamy et al).

Formula I

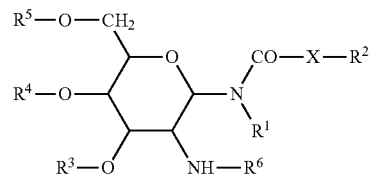

In the structure of Formula I, R1 is hydrogen, or a saturated alkyl radical having up to 20 carbon atoms; X is —CH2-, —O— or —NH—; R2 is hydrogen, or a saturated or unsaturated alkyl radical having up to 20 carbon atoms; R3, R4, and R5 are independently hydrogen, —SO42-, —PO42-, —COC1-10 alkyl; R6 is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers.

In one embodiment, the suitable glycolipid is N-(2-Deoxy-2-L-leucylamino-b-D-glucopyranosyl)-N-octadecyldodecanoylamide or an acetate thereof, also known by the trade name Bay R1005®.

In some embodiments the adjuvant may comprise an immunostimulatory oligonucleotide. Suitable immunostimulatory oligonucleotides include ODN (DNA-based) and ORN (RNA-based) oligonucleotides, which may have modified backbone including, without limitations, phosphorothioate modifications, halogenations, alkylation (e.g., ethyl- or methyl-modifications), and phosphodiester modifications. In some embodiments, poly inosinic-cytidylic acid or derivative thereof (poly I:C) may be used. In a set of embodiments, the oligonucleotides of the instant invention contain palindromes, and preferably, are capable of forming hairpin-like secondary structures comprising a stem and a loop. In certain embodiments, the immunostimulatory oligonucleotides are single-stranded, though they may contain palindromic structures and thus form double-stranded, e.g., stem-loop, structures. Several classes of immunostimulatory oligonucleotides are known in the art.

The amount of immunostimulatory oligonucleotide for use in the adjuvant depends upon the nature of the immunostimulatory oligonucleotide used, and the intended species. However, they are generally used in an amount of about 1 microgram to about 20 mg per dose. They also are used in an amount of about 1 microgram to about 10 mg per dose, about 1 microgram to about 5 mg per dose, about 1 microgram to about 4 mg per dose, about microgram to about 3 mg per dose, about 1 microgram to about 2 mg per dose, and about 1 microgram to about 1 mg per dose.

In some embodiments the adjuvant may comprise an aluminum-based component. Aluminum is a known adjuvant or a component of adjuvant formulations, and is commercially available in such forms as alhydrogel (Brenntag; Denmark) or REHYDRAGEL® (Reheis, Inc; New Jersey). REHYDRAGEL® is a crystalline aluminum oxyhydroxide, known mineralogically as boehmite. It is effective in vaccines when there is a need to bind negatively-charged proteins. The content of Al2O3 ranges from 2% to 10% depending on grade, and its viscosity is 1000-1300 cP. Generally, it may be described as an adsorbent aluminum hydroxide gel.

In some embodiments the present invention includes, but is not limited to, an immunogenic composition comprising an isolated HeV or NiV G protein capable of inducing the production of a cross-reactive neutralizing anti-serum against multiple strains of HeV and/or NiV in vitro, and an adjuvant comprising polyoxyethylene-polyoxypropylene block copolymer (Pluronic® L121), squalane, polyoxyethylene sorbitan monooleate (Tween® 80), and a buffered salt solution, for example wherein the composition contains: 5, 50, 100, or 250 µg of soluble HeV or NiV G protein, and appropriate amounts of the adjuvant components.

In another embodiment of the invention, the vaccine and immunogenic compositions may be part of a pharmaceutical composition. The pharmaceutical compositions of the present invention may contain suitable pharmaceutically acceptable carriers comprising excipients and auxiliaries that facilitate processing of the active compounds into preparations that can be used pharmaceutically for delivery to the site of action.

Excipients

The immunogenic and vaccine compositions of the invention can further comprise pharmaceutically acceptable carriers, excipients and/or stabilizers (see e.g. Remington: The Science and practice of Pharmacy (2005) Lippincott Williams), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as Mercury((o-carboxyphenyl)thio)ethyl sodium salt (THIOMERSAL), octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG), TWEEN or PLURONICS.

The compositions of the invention can be in dosages suspended in any appropriate pharmaceutical vehicle or carrier in sufficient volume to carry the dosage. Generally, the final volume, including carriers, adjuvants, and the like, typically will be at least 1.0 ml. The upper limit is governed by the practicality of the amount to be administered, generally no more than about 0.5 ml to about 2.0 ml.

EXAMPLES

For use in Examples 1-3, *P. multocida* (P1062) serogroup A serotype 3, a well characterized bovine isolate (Abrahante, et al., Draft genome sequence of *Pasteurella multocida* isolate P1062, isolated from Bovine Respiratory Disease. Genome Announc. 2015. pii: e00058-12. doi: 10.1128/genomeA.00058-12) was used to construct the mutated *P. multocida* containing a temperature-sensitive plasmid origin of replication (see Briggs and Tatum, Generation and molecular characterization of new temperature-sensitive plasmids intended for genetic engineering of Pasteurellaceae. Appl. Environ. Microbiol. 2005. 71:7187-7195). An acapsular mutant was produced by introducing a deletion mutation in hyaC, which encodes UDP-glucose dehydrogenase enzyme. A second *P. multocida* mutant was then produced by inactivating nanP, whose gene product is required for uptake of environmentally procured sialic acid, which renders the mutant devoid of sialic acid modification. The double deletion *P. multocida* ΔhyaC ΔnanP mutant was constructed to serve as a live attenuated vaccine candidate to mitigate BRD.

*P. multocida* strain P-1062 is a bovine lung isolate of Carter Heddleston type A:3. *P. multocida* was grown on Columbia blood agar base plates (Difco Lab., Detroit, MI). Invitrogen™ One Shot™ Top10 Chemical-Competent *E. coli* (ThermoFischer Scientific, Waltham, MA) was used for plasmid propagation and cloning and was also cultured on Columbia blood agar base plates.

All primers were custom synthesized by Integrated DNA Technologies, Inc. (Coralville, IA). Whole *P. multocida* P-1062 cells were used as template in the PCR reactions which were performed using ThermoFischer Scientific's EasyStart™ PCR Mix-in-a-Tube and the manufacturer's recommended protocol (Molecular BioProducts, San Diego, CA). A GeneAmp 9600 PCR System thermocycler (Perkin Elmer Corp., Norwalk, CT) was used to generate all the PCR-amplified products. Reaction conditions entailed 30 cycles at annealing temperatures according to the melting temperatures of the various primer pairs listed in Table 1, infra. Listed below in Table 1 are the primer names, with assigned SEQ ID NOs, and the associated annealing temperatures (in ° C.); followed by a depiction of the actual nucleotide sequence with indicated restriction recognition sites underlined.

TABLE 1

PRIMER CHARACTERISTICS

1062 Bam-nanP-F (SEQ ID NO: 13), annealing temp 61° C.
5'-AAAGGATCCGCGGATGTGATAGTTTTGACAT-3' (BamH1)

1062 Sal-nanP-R (SEQ ID NO: 14), annealing temp 60° C.
5'-AAAGTCGACACTGTCGGTGAGCTTG-3' (SalI)

1062 Bam-hyaC-F (SEQ ID NO: 15), annealing temp 57° C.
5'-AAAGGATCCATGTTGATAAGAATCATCTTACAC-3' (BamH1)

1062 Pst-hyaC-R (SEQ ID NO: 16), annealing temp 63° C.
5'-AAACTGCAGTGGCGTTGCGATGATGA-3' (Pst1)

1062 Pst-hyaC-F (SEQ ID NO: 17), annealing temp 57° C.
5'-AAACTGCAGCAAGTTTCGGCTATGGCG-3' (Pst1)

1062 Sal-hyaC-R (SEQ ID NO: 18), annealing temp 61° C.
5'-AAAGTCGACCGCACGATAACGATATGTCTG-3' (Sal1)

Example 1. Construction of *P. multocida* (P1062) ΔnanP

Figure 4:
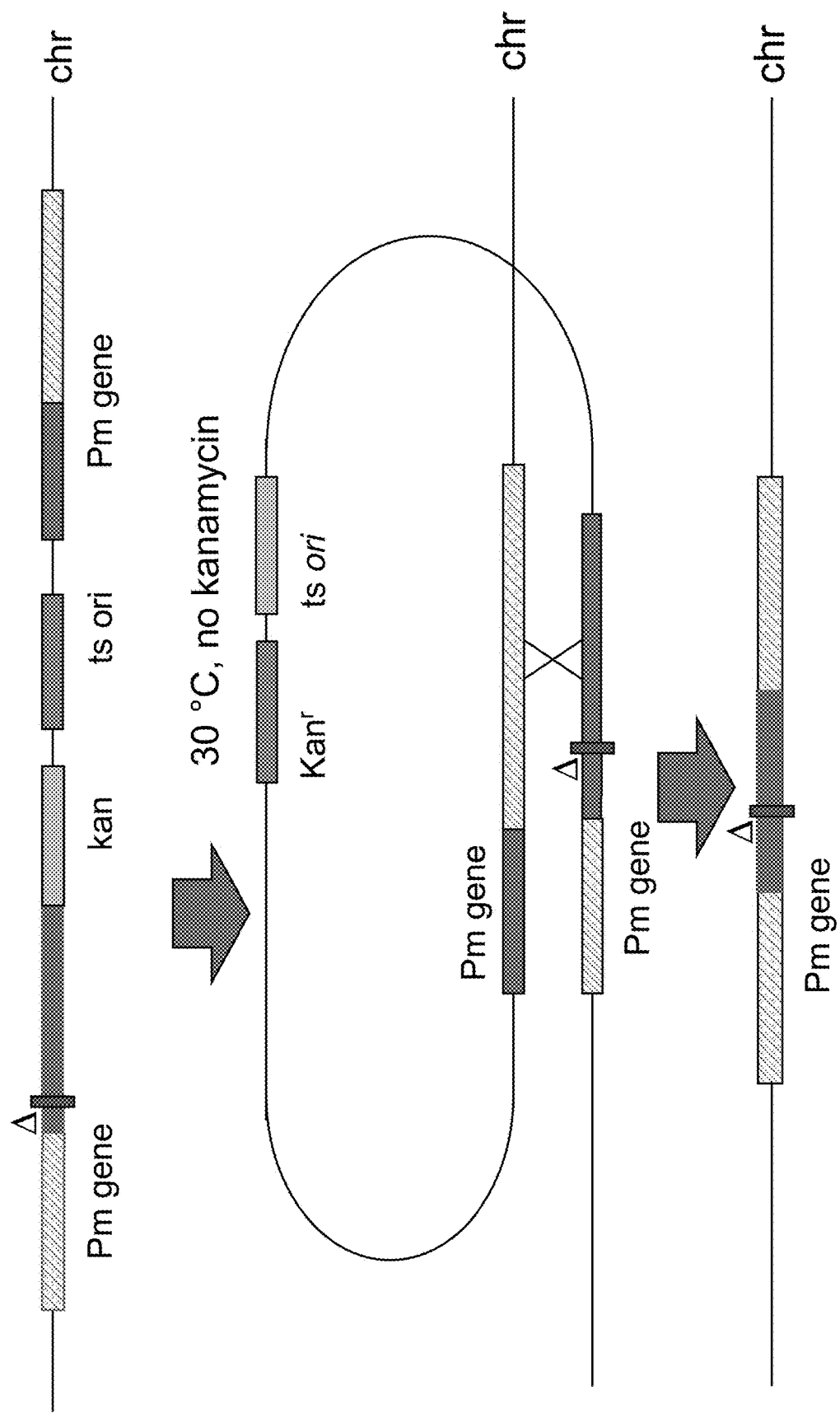
FIG. 4 shows the removal of the replacement plasmids from *P. multocida* genome.

The ΔnanP replacement arms used to generate the mutation in *P. multocida* P-1062 were synthesized by PCR using primers 1062 Bam-nanP-F (SEQ ID NO: 13) and 1062 Sal-nanP-R (SEQ ID NO: 14). See Table 2, supra. The obtained PCR fragment, contained within SEQ ID NO: 5, of approximately 2850 base pairs, was purified with QIAquick™ spin columns (Qiagen Inc., Valencia, CA), and sequenced with fluorescent terminators by cycle sequencing with an Applied Biosystems model 373 DNA sequencer (DNA facility at Iowa State University, Ames, IA). The purified PCR product was subjected to BamH1 and Sal I digestion, phenol chloroform extraction, and ethanol precipitation. The recovered fragment (contained within SEQ ID NO: 5) was then inserted into the corresponding sites of plasmid pBCSK (Stratagene Inc., LaJolla CA) using T7 DNA ligase. The ligated product was introduced into One Shot™ Top10 Chemical-Competent *E. coli* cells (ThermoFischer Scientific, Waltham, MA) which were then plated on Columbia blood agar containing 34 micrograms chloramphenicol, and cultured overnight at 37° C. Colonies were assessed for desired product by PCR analysis, and colonies exhibiting a product consistent with the expected nanP insert were propagated in Columbia broth containing 34 micrograms chloramphenicol. The recombinant plasmid, pBCSKnanP, was purified using the Qiaprep™ Spin Miniprep system (Qiagen, Germantown, MD). An in-frame deletion within nanP was produced by digestion with EcoR1 followed by ligation with T7 ligase to produce a 708 bp in-frame deletion (FIG. 1). SEQ ID NO: 7 is the ΔnanP with surrounding operon sequences present in SEQ ID NO: 5. The DNA sequence of ΔnanP is set forth in SEQ ID NO: 3 and amino acid sequence of ΔnanP is set forth in SEQ ID NO: 4. Unmodified nanP DNA sequence is set forth in SEQ ID NO: 1 and the unmodified amino acid sequence is set forth in SEQ ID NO: 2. SEQ ID NOs: 19 and 20 are a partial DNA and amino acid sequences of ΔnanP surrounding the site of the deleted sequences.

The ligated product with BamHI and SalI recognition sequences (contained within SEQ ID NO: 7) was transformed into Invitrogen™ One Shot™ Top10 Chemical-Competent *E. coli* (ThermoFischer Scientific, Waltham, MA) and propagated on Columbia agar plates containing 34 micrograms chloramphenicol. Plasmid pBC+ΔnanP was recovered and purified as described infra, then was digested with BamHI and ligated with a Tn903 kanamycin resistance element to produce plasmid pBC+ΔnanP+kan. Gene replacement mutants of *P. multocida* P1062 (bovine, serogroup A:3) were generated using the temperature-sensitive plasmid origin-of-replication from pCT109GA189, described in Briggs and Tatum (2005). The replacement plasmid, pTS+Kan+ΔnanP, was generated by joining BssHII digested plasmids pBC+ΔnanP+kan and pBC TSori (pBC containing the temperature sensitive origin of replication from pCT109GA189). Assembly of the replacement plasmid, pTS+Kan+ΔnanP, is shown in FIG. 2.

pTS+Kan+ΔnanP was then used to generate the *P. multocida* ΔnanP mutant using a stepwise procedure. Initially, the replacement plasmid, pTS+Kan+ΔnanP, was electroporated into *P. multocida* P-1062. Cells were made electrocompetent by growing them to logarithmic phase in 100 ml Columbia broth at 37° C. with gentle shaking. *P. multocida* were pelleted by centrifugation at 5000×G and washed in 100 ml 272 mM sucrose at 0° C. The pellet was suspended in equal volume of 272 mM sucrose at 0° C. Competent *P. multocida* (100 microliters) were placed into 0.1 cm electroporation cuvettes and mixed with 100 ng of replacement plasmid DNA. The cells were electroporated (Gene Pulser, BioRad, Richmond, CA) at 18,000 V/cm and 800 ohms yielding time constants ranging from 11-12 msec. Immediately after electroporation the *P. multocida* cells were resuspended in 1.0 ml Columbia broth at 0° C. Recovery was for 2 hours at 30° C. The suspension was spread (100 microliters/plate) onto Columbia agar plates containing 25 microgram/ml kanamycin. Transformed *P. multocida* colonies arose on selective plates which were incubated at the permissive temperature (30° C.) for autonomous plasmid replication. The colonies were individually amplified in selective broth (25 microgram/ml kanamycin) at 30° C., then growth was spread onto selective plates and incubated at 40° C., the non-permissive temperature for autonomous temperature-sensitive plasmid replication. Because the plasmid replicates poorly at this temperature, it must integrate into bacterium's chromosome to survive and render the bacterium resistant to kanamycin. Primarily, single-crossover mutant colonies arise by means of homologous recombination when cells are cultured at high temperature (40° C.). See FIG. 3.

Randomly selected putative single-crossover mutant colonies were then transferred to broth, without antibiotic selection, and incubated at the permissive temperature (30° C.) for autonomous plasmid replication. After three serial passages at permissive temperature (30° C.) in 2 ml broth, a loop of culture was spread onto Columbia blood agar plates, and incubated at 37° C. Most colonies arising after serial passage of the single-crossover mutants were found to be devoid of plasmid. During this step, instability caused by the active plasmid origin contained on the chromosome increased resolution of replacement plasmid from the chromosome and, depending where homologous recombination occurred, either wild-type or ΔnanP mutant progeny arose. See FIG. 4.

Figure 5B:
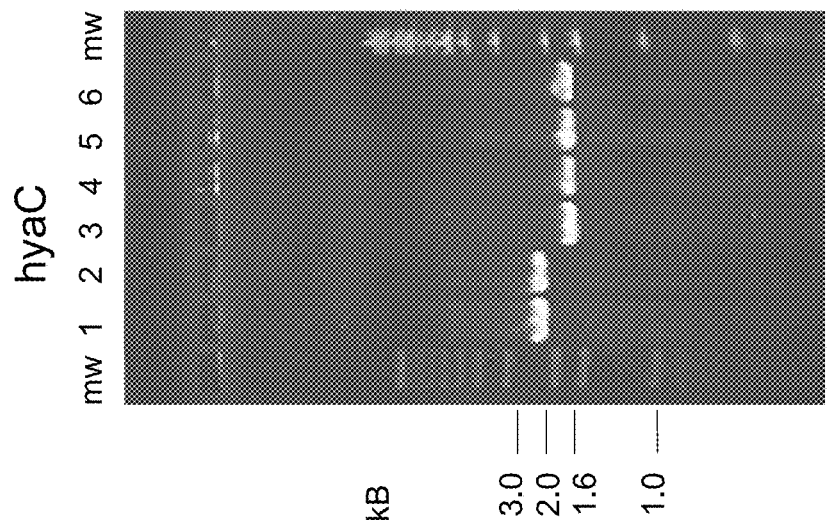
FIG. 5B shows a gel confirming the presence of the ΔhyaC mutation. Lanes 1 and 2: wildtype *P. multocida* 1062 amplified product; lanes 3 and 4 ΔhyaC *P. multocida* amplified product; lanes 5 and 6: ΔnanP ΔhyaC *P. multocida* amplified product.
Figure 5A:
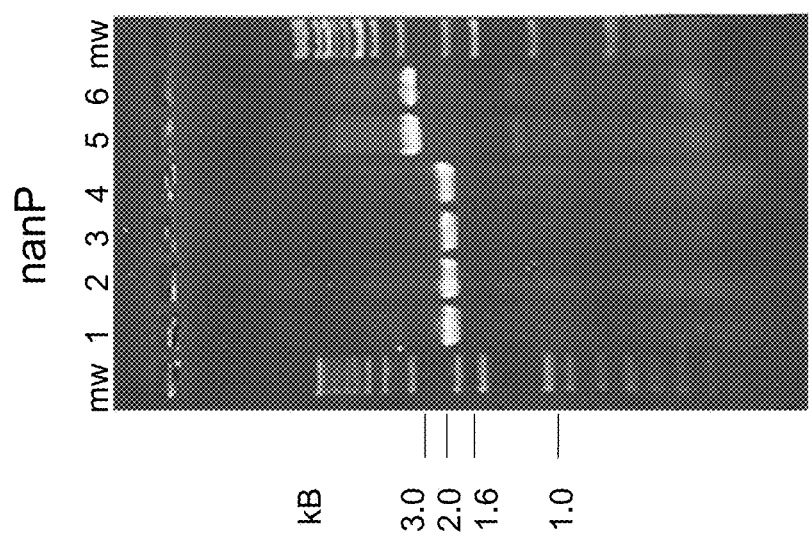
FIG. 5A shows a gel confirming the presence of the ΔnanP mutation. Lanes 1 and 2: ΔnanP *P. multocida* amplified product; lanes 2 and 3: ΔnanPΔhyaC *P. multocida* amplified product; lanes 5 and 6: wildtype *P. multocida* 1062 amplified product.

PCR was then used to identify *P. multocida* ΔnanP deletion mutants, as shown in FIG. 5A. Briefly, primers specific for nanP were used to amplify DNA from colonies expected to express ΔnanP; ΔhyaCΔnanP; or wildtype nanP. In FIG. 5A, lanes 1 and 2 are PCR products from colonies expressing ΔnanP; lanes 3 and 4 are from colonies expressing ΔhyaCΔnanP; and lanes 5 and 6 are from colonies expressing wildtype nanP. PCR analysis showed that the selected clones possessing ΔnanP also were devoid of the Tn903 kanamycin resistance element and the TS origin of replication. The presumptive, *P. multocida* ΔnanP mutants were assessed for sialic acid uptake using The QuantiChrom™ Sialic Acid Assay Kit (BioAssay Systems, Hayward, CA), and those clones possessing the ΔnanP mutation, unlike the parent, were unable to take up sialic acid from growth media. Uptake of free sialic acid is rapid and nearly complete in cultures of the parent *P. multocida*, whereas no uptake of sialic acid was detected from mutants, indicating that the nanP gene product is necessary for uptake of free sialic acid.

Example 2. Construction of *P. multocida* (P1062) ΔhyaC

Figure 6:
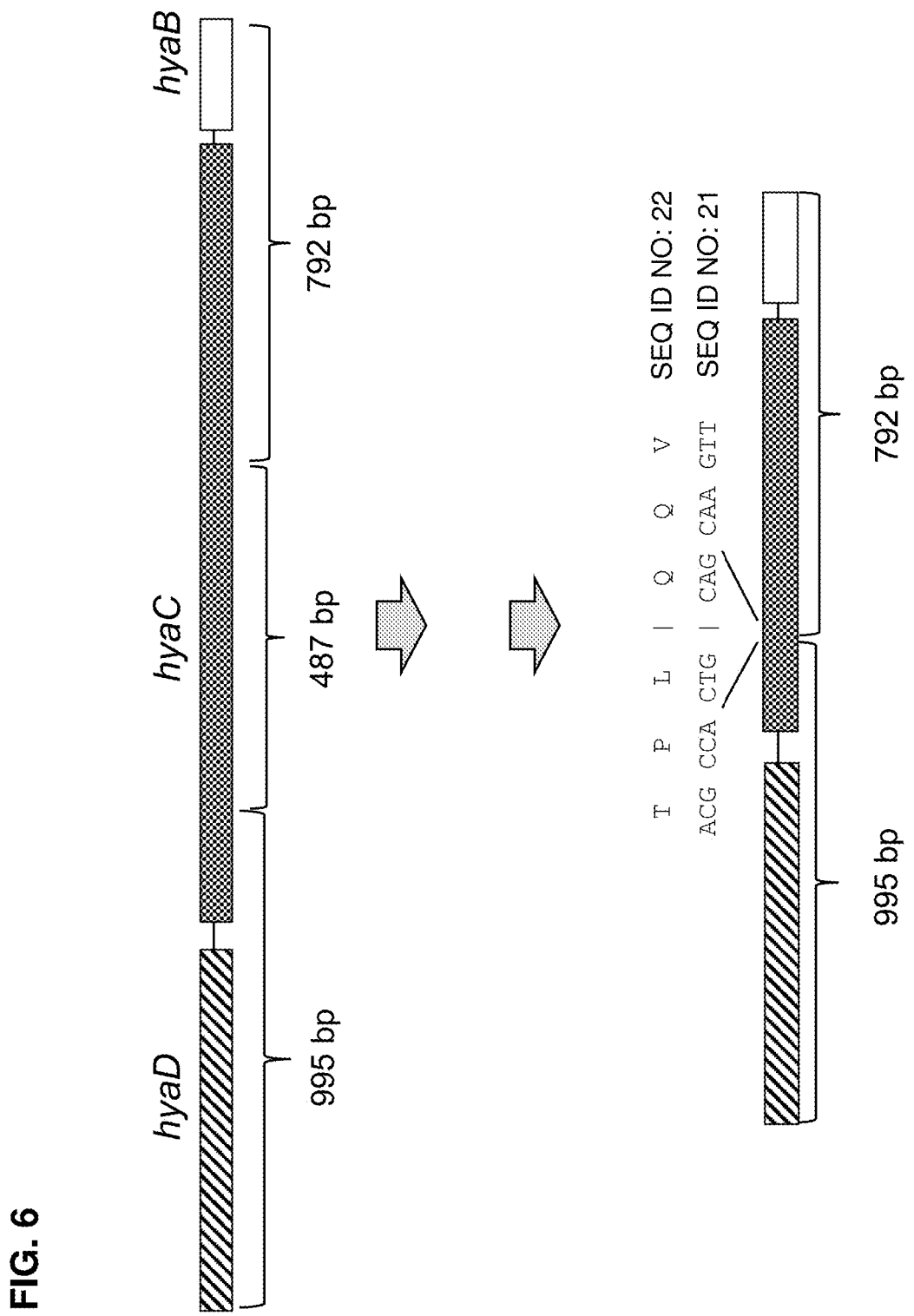
FIG. 6 shows the general construction of the ΔhyaC mutation in *P. multocida*.

Wild-type hyaC DNA sequence is shown in SEQ ID NO: 8; and amino acid sequence is shown in SEQ ID NO: 9. The ΔhyaC replacement arms used to generate the hyaC mutation in *P. multocida* P-1062 were synthesized by PCR using two sets of primers (i) 1062 Bam-hyaC-F (SEQ ID NO: 15) and 1062 Pst-hyaC-R (SEQ ID NO: 16) and (ii) 1062 Pst-hyaC-F (SEQ ID NO: 17) and 1062 Sal-hyaC-R (SEQ ID NO: 18). See Table 1, supra. For the 5' arm primer pair, primer 1062 Bam-hyaC-F binds to nucleotides 41-64 of SEQ ID NO: 10, and primer 1062 Pst-hyaC-R binds to nucleotides 1019-1035 of SEQ ID NO: 10. For the 3' primer pair, primer 1062 Pst-hyaC-F binds to nucleotides 1523-1540 of SEQ ID NO: 10, and primer 1062 Sal-hyaC-R binds to nucleotides 2294-2314 of SEQ ID NO: 10. SEQ ID NO: 10 contains wild-type hyaC DNA sequence and approximately 786 bp upstream to hyaC and approximately 544 bp downstream to hyaC. Each primer pair set are individually hybridized to *P. multicoda* DNA, and PCR was performed to generate two amplicons, an upstream arm and a downstream arm. The amplicons were purified with QIAquick™ spin columns (Qiagen Inc., Valencia, CA) and sequenced with fluorescent terminators by cycle sequencing with an Applied Biosystems model 373 DNA sequencer (DNA facility at Iowa State University, Ames, IA). The purified upstream arm amplicon was subjected to BamH1 and Pst I double-digestion, and the downstream arm amplicon was subjected to PstI and SalI double-digestion. After phenol chloroform extraction and ethanol precipitation, the recovered amplicons were sequentially inserted into the corresponding sites (BamH1 and SalI) of plasmid pBCSK (Stratagene Inc., LaJolla CA) using T7 DNA ligase, and the open ends of the amplicons were ligated together at their PstI site; generating pBC+ΔhyaC. The mutated hyaC contains a 487 bp deletion, and a PstI recognition site is formed at the junction of the two replacement arm amplicons. The deletion also resulted in a frame shift of the coding sequence. SEQ ID NO: 12 is the nucleotide sequence of ΔhyaC. When transcribed, the ΔhyaC encodes a non-functional protein having the amino acid sequence of SEQ ID NO: 11. SEQ ID NO: 6 is the DNA of ΔhyaC and surrounding nucleotides. SEQ ID NOs: 21 and 22 are the DNA and amino acid sequences surrounding the deletion site in ΔhyaC. See FIG. 6.

Each ligated product was introduced into Invitrogen™ One Shot™ Top10 Chemical-Competent *E. coli* (ThermoFischer Scientific, Waltham, MA), plated on Columbia blood agar containing 34 microgram chloramphenicol, and cultured overnight at 37° C. Colonies were assessed for desired product by PCR analysis, and a colony possessing the hyaC upstream arm amplicon and downstream arm amplicon was propagated in Columbia broth containing 34 microgram chloramphenicol. The recombinant plasmid, pBC+ΔhyaC, was purified using the Qiaprep™ Spin Miniprep system (Qiagen, Germantown, MD) and then sequenced as previously described.

Figure 2:
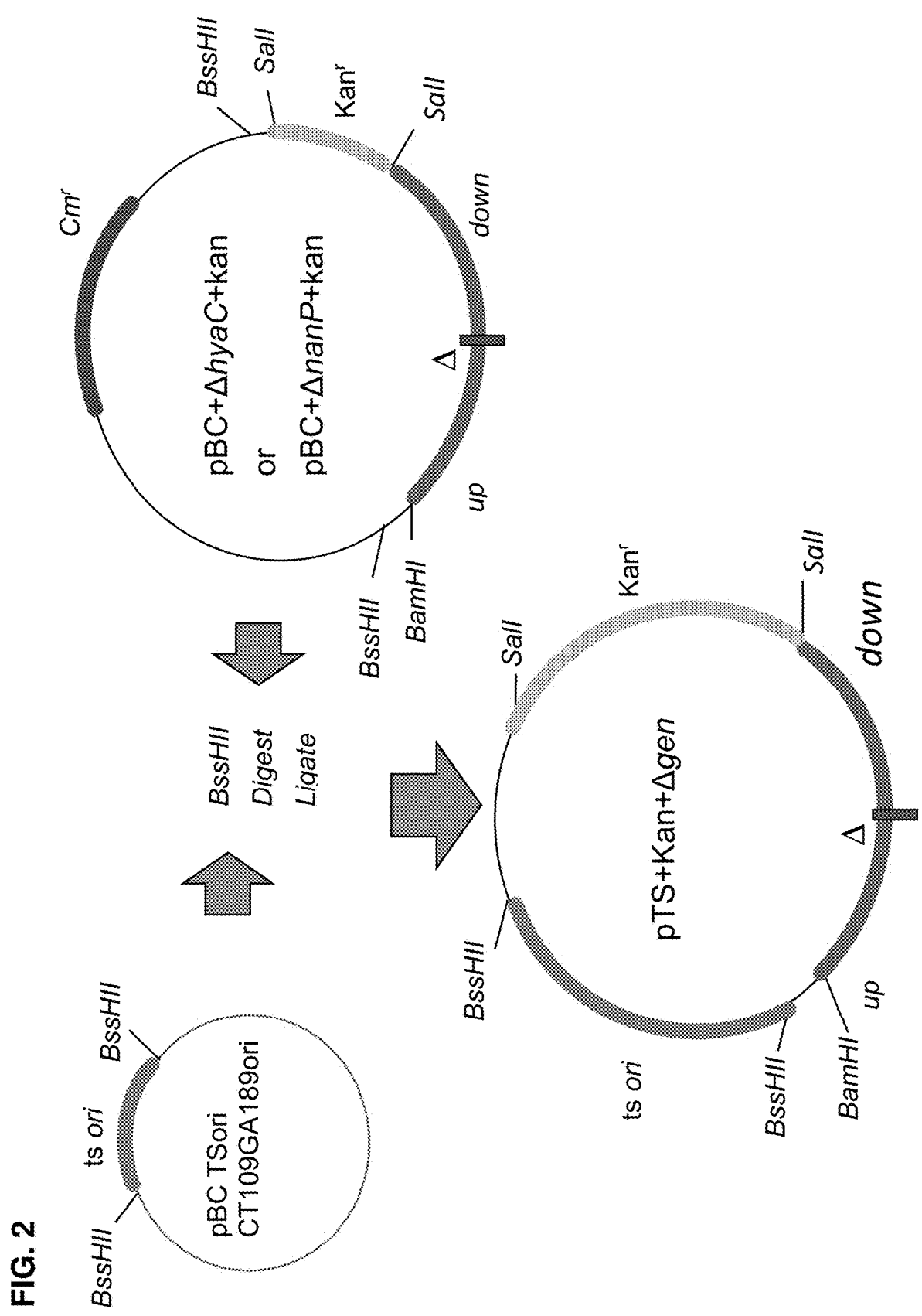
FIG. 2 shows the general construction of the replacement plasmids containing a temperature sensitive origin of replication and either the ΔnanP mutation or the ΔhyaC mutation in *P. multocida*.
Figure 3:
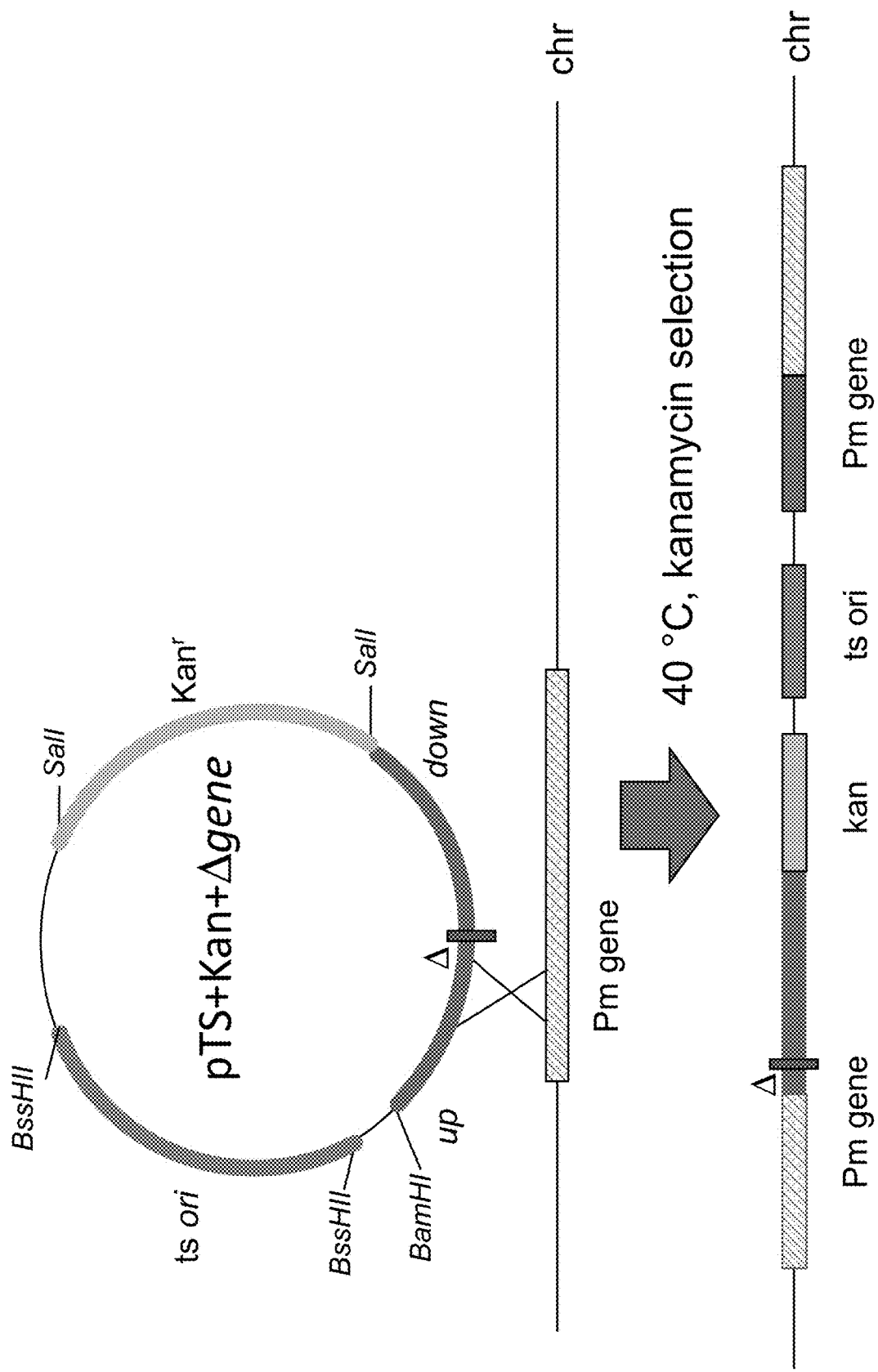
FIG. 3 shows the integration of the replacement plasmids into *P. multocida* genome.

Next, pBC+ΔhyaC was digested with BamHI, treated with shrimp alkaline phosphatase (New England BioLabs Inc., Ipswich, MA), phenol chloroform extracted, and ethanol precipitated. The recovered BamHI-digested plasmid was ligated with a Tn903 kanamycin resistance element also possessing BamHI overhanging ends to produce pBC+ΔhyaC+kan. The replacement plasmid pTS+Kan+ΔhyaC, which was used to generate the *P. multocida* ΔhyaC mutant, was constructed by joining BssHII-digested plasmids pBC+ΔhyaC+kan and pBC TSori (pBCSK containing the temperature sensitive origin-of-replication from pCT109GA189). See also FIG. 2.

pTS+Kan+ΔhyaC was used to generate the *P. multocida* ΔhyaC mutant via a stepwise procedure using the protocols described in Example 1, supra. See also FIGS. 3 and 4. PCR analysis was used to identify *P. multocida* ΔhyaC deletion mutants shown in FIG. 5B. Briefly, primers specific for hyaC were used to amplify DNA from colonies expected to express ΔhyaC; ΔhyaCΔnanP; or wildtype hyaC. In FIG. 5B, lanes 1 and 2 are PCR products from colonies expressing wildtype hyaC; lanes 3 and 4 are from colonies expressing ΔhyaC; and lanes 5 and 6 are from colonies expressing ΔhyaCΔnanP. Selected clones possessing ΔhyaC also were shown by PCR analysis to be devoid of the Tn903 kanamycin resistance element and the temperature-sensitive origin of replication. The *P. multocida* ΔhyaC colonies did not produce capsule and were phenotypically very distinct from the wild-type parent. The acapsular mutants were easily distinguished from the wild-type parent visually and, unlike the parent, they were non-mucoid and non-iridescent when viewed with white light.

Example 3. Construction of *P. multocida* (P1062) ΔnanP ΔhyaC Double Mutant

The *P. multocida* (P1062)ΔnanPΔhyaC double mutant was constructed by transforming pTS+Kan+ΔhyaC into *P. multocida* (P1062) ΔnanP mutant described supra using the protocols described supra. This order for constructing the *P. multocida* ΔnanPΔhyaC double mutant was primarily because a ΔhyaC mutant, lacking capsule, is phenotypically identifiable on culture plates.

Example 4. Evaluation of the Safety of ΔhyaC/nanP *Pasteurella multocida* Vaccine when Administered Intranasally to 14-Day Old Calves The objective of the study was to evaluate the safety of two dose levels of ΔhyaC/ΔnanP *Pasteurella multocida*

("PM") when administered intranasally (one nostril) to calves at 14 days of age. Thirty-six male Holstein calves were randomly assigned to one of two treatment groups (T01 and T02) or two NT groups (NT1-NT2; no treatment).

T01 was provided as lyophilized ΔhyaC/ΔnanP PM, with a target of $1\times10^9$ CFU/dose, actual at start: $1.1\times10^9$ CFU/dose, end: $1.1\times10^9$ CFU/dose. Similarly, T02 was provided as lyophilized ΔhyaC/nanP PM, with a target of Target: $1\times10^5$ CFU/dose, actual at start: $1.7\times10^5$ CFU/dose, end: $1.7\times10^5$ CFU/dose). Animals were housed in individual pens, with treatment groups T01 and NT1 housed together, and T02 and NT2 housed together. Five calves each in T01 and T02 were assigned to necropsy days 3, 7, or 14. All NT animals were euthanized on day 14. Rectal temperatures were collected on day −2, and both clinical observations were recorded on days −1 through 14. Nasal swabs were collected on days −1, 1-5, 8, 11, and 14. At necropsy, lungs were scored for percent of lesions, and swabs were collected from the lung, trachea, and left and right inner ears. Joint fluid and bronchial-alveolar lavage (BAL) samples were also collected.

The ΔhyaC/ΔnanP P. multocida mutant was determined, by this study, to be safe when administered intranasally in young calves. This was supported by the lack of persistent clinical signs, and no recovery of P. multocida from any of the necropsy swabs. No "droopy ears" or positive ear cultures were observed during this study, which was a constant safety issue with previously tested isolates. As presented below, no P. multocida recovered for any lung or bronchial-alveolar lavage (BAL) samples, Tables 2 and 3.

TABLE 2

LUNG SUAB CULTURES

| Treatment Number | Lung Swab Day of Study | Presence of P. multocida (% Positive) | (N) |
|---|---|---|---|
| NT1 | 14 | 0.0 | 3 |
| NT2 | 14 | 0.0 | 3 |
| T01 | 3 | 0.0 | 5 |
|  | 7 | 0.0 | 5 |
|  | 14 | 0.0 | 5 |
| T02 | 3 | 0.0 | 5 |
|  | 7 | 0.0 | 5 |
|  | 14 | 0.0 | 5 |

TABLE 3

Bronchial-Alveolar Lavage (BAL) Cultures

| Treatment Number | BAL Day of Study | Presence of P. multocida (% Positive) | (N) |
|---|---|---|---|
| NT1 | 14 | 0.0 | 3 |
| NT2 | 14 | 0.0 | 3 |
| T01 | 3 | 0.0 | 5 |
|  | 7 | 0.0 | 5 |
|  | 14 | 0.0 | 5 |
| T02 | 3 | 0.0 | 5 |
|  | 7 | 0.0 | 5 |
|  | 14 | 0.0 | 5 |

Example 5. Evaluation of Shed and Spread of a Modified Live Pasteurella multocida hyaC/nanP Administered Subcutaneously in Calves This study was conducted to demonstrate the nasal shed of a modified live deletion mutant Pasteurella multocida Master Seed Bacteria (MSB), "following subcutaneous administration and possible spread to susceptible calves, in accordance with Veterinary Service Memorandum 800.201. To conserve the MSB, an additional passage to the P. mult 1062: hyaC/nanP MSB, was prepared for use in this study.

Fourteen, five-week-old, Holstein bull calves, seronegative to and free of P. multocida colonization in the nasal passage were randomized to treatment groups T01 (n=7; subcutaneous administration; P. multocida hyaC/nanP), or NT1 (n=7; no treatment controls). The animals were commingled in one Biosafety Level 2 room for the duration of the study. Blood samples were collected on days −5 and 0, and nasal swabs and naso-pharyngeal swabs were collected on days −5 and 0 through 21. Rectal temperatures and clinical observations were recorded on days −2 through 21.

No P. multocida was ever isolated from nasal or naso-pharyngeal swabs from either treatment group during the study. Five T01 and five NT1 animals had at least one day of elevated (104° F.) temperatures between days 8 and 17, and one T01 and one NT1 animal had temperatures 04° F. on day 2. All animals were scored as normal for nasal discharge and ear droop for the study duration. There were minimal numbers of calves that were scored for mild attitude, cough, lameness, and respiratory effort. Two NT1 calves were scored for mild attitude, and one NT1 calf was scored for mild cough and respiratory effort. In the T01 group, two calves were scored for mild or moderate lameness, and one T01 calf was scored for mild respiratory effort. There was no shed of P. multocida hyaC/nanP by inoculated calves, and there was no spread to non-inoculated contact control animals (see Tables 4 and 5, for example). The safety of the P. multocida hyaC/nanP was also demonstrated in 5-week-old calves.

TABLE 4

Presence of P. multocida in Nasal Swabs

| Treatment Number | Positive Number | % | Total Observations Number |
|---|---|---|---|
| NT1 | 0 | 0.0 | 7 |
| T01 | 0 | 0.0 | 7 |

TABLE 5

Presence of P. multocida in Naso-pharyngeal Swabs

| Treatment Number | Positive Number | % | Total Observations Number |
|---|---|---|---|
| NT1 | 0 | 0.0 | 7 |
| T01 | 0 | 0.0 | 7 |

Example 6. Reversion to Virulence Evaluation of a Modified Live Pasteurella multocida hyaC/nanP in Calves As described previously, one of the preferred embodiments of the invention is to add a modified-live Pasteurella multocida ΔhyaC/ΔnanP deletion mutant to Bovishield Gold-One Shot®, Zoetis (Bovine Rhinotracheitis-Virus Diarrhea-Parainfluenza3-Respiratory Syncytial Virus Vaccine, Modified Live Virus-*Mannheimia Haemolytica* Toxoid). The recombinant modified live *P. multocida* hyaC/nanP contains deletions of the hyaC and nanP genes. The Center for Veterinary Biologics (CVB) Veterinary Services Memorandum 800.201 requires a reversion to-virulence study to evaluate the safety and stability of a new modified live vaccine. This study was thus conducted to demonstrate a lack of reversion to virulence of a modified live *Pasteurella multocida* 1062: ΔhyaC/ΔnanP bacteria following serial backpassage in susceptible calves.

The *Pasteurella multocida* 1062: ΔhyaC/ΔnanP Master Seed Bacteria+1 (MSB+1) was evaluated for its safety in susceptible calves in five backpassages. All animals enrolled on study were healthy five-week-old Holstein calves, negative in naso-pharyngeal swabs for *Pasteurella multocida* (*P. multocida*) as well as seronegative for antibodies to *P. multocida* outer membrane proteins (OMP; serum S/P ratio of <0.8) on day 0. Calves were housed in individual pens for the duration of the study. Animals were observed for clinical signs of attitude, cough, drooped ear, lameness, nasal discharge, and respiratory effort daily on days −2 through 21; rectal temperatures were also collected daily. Serum was collected on days −5 and 0; naso-pharyngeal swabs were collected on days −5 and 0 through 21. During backpassage #5, two animals (one inoculated and one non-inoculated control) were observed for clinical observations and rectal temperatures through day 27 and had naso-pharyngeal swabs collected on days 22 through 25 to determine when shedding ceased.

In the initial backpassage, seven calves were inoculated intranasally with 2 mL of the *P. multocida* 1062: ΔhyaC/ΔnanP MSB+1 at a concentration of $2.56 \times 10^9$ CFU/dose. Three calves served as non-inoculated controls. Animals in subsequent backpassages (#2 through #5) were inoculated with 2 mL (1 mL per nares) of pooled nasal secretions from the previous backpassage. Seven animals were inoculated in backpassage #2, with two animals serving as non-inoculated controls. Ten animals were inoculated in backpassages #3 through #5; and two to three animals served as non-inoculated control animals. Due to the identification of a wild-type *P. multocida* during PCR analysis of the sole positive sample in backpassage #4, this backpassage was repeated using the remaining aliquots of nasal secretions from backpassage #3. The wild-type *P. multocida* was later determined via whole genome sequence (WGS) to be the vaccine parent strain (*P. multocida* 1062) that was used as the positive control in the PCR assay; its presence was due to laboratory contamination that occurred during the colony selection for the PCR analysis. At least one inoculated animal had *P. multocida* 1062: ΔhyaC/ΔnanP positive naso-pharyngeal swabs during each backpassage. There were 4/7 inoculated animals with positive naso-pharyngeal swabs during backpassage #1; 1/7 in backpassage #2; 6/10 in backpassage #3, and 1/10 animals in backpassage #4 (original), backpassage #4 (repeat), and backpassage #5. The *P. multocida* 1062: ΔhyaC/ΔnanP inoculum counts decreased from $2.56 \times 10^9$ CFU/dose in the initial backpassage to $4.20 \times 10^3$ CFU/dose in the final backpassage.

Moderate or severe clinical signs were not observed in any animals during the study (score=2 or greater). Mild abnormal clinical signs (score=1) and temperatures above 104.0° F. were observed in at least one calf in all backpassages; both non-inoculated and/or inoculated animals were affected depending on the backpassage. The abnormal clinical signs observed are not uncommon in colostrum deprived five-week-old calves. The stability of the hyaC and nanP deletions was confirmed by evaluating colonies via PCR from the first and last day of positive *P. multocida* samples from each positive calf in each backpassage; all positive samples were confirmed to be the vaccine strain. The minimal numbers of animals with abnormal clinical signs and fever, as well, as the stability of the gene deletions, demonstrates safety of the *P. multocida* 1062: ΔhyaC/ΔnanP MSB+1 and a lack of reversion to virulence of the *Pasteurella multocida* 1062: ΔhyaC/ΔnanP Master Seed Bacteria.

Example 7. Additional Investigation for Reversion to Virulence Evaluation of a ΔhyaC/ΔnanP *Pasteurella multocida* in Calves This study was conducted to demonstrate the lack of reversion to virulence of a modified live ΔhyaC/ΔnanP *P. multocida* following serial backpassage in 6- to 7-day-old colostrum deprived calves in accordance with Veterinary Service Memorandum 800.201 and VICH Guidelines 41. ΔhyaC/ΔnanP *P. multocida* Masterseed+1 was evaluated for its safety in susceptible calves in a total of four backpassages. All animals enrolled in the study were 6- to 7-day-old colostrum deprived Holstein calves that were seronegative to *P. multocida* Outer Membrane Protein (OMP) and were negative for *P. multocida* in nasal secretions. Calves were housed in individual pens for the duration of the study. Animals were observed for clinical signs of attitude, nasal discharge, respiratory effort, lameness, cough and ear droop and rectal temperatures were collected from days −4 through 21 for each backpassage. Serum was collected on days −5 and day 0; nasal-pharyngeal swabs were collected on day −5 and on days 0 through 21 and quantitative counts of *P. multocida* were conducted. Presence of ΔhyaC/ΔnanP gene deletion in any *P. multocida* isolated was confirmed by PCR.

In the initial backpassage, seven calves were inoculated intranasally in one nostril with 2 mL of the ΔhyaC/ΔnanP *P. multocida* at a concentration of $2.4 \times 10^9$ to $2.6 \times 10^9$ CFU/dose (start and end of inoculation counts, respectively). Subsequent passages were inoculated with 2 mL of pooled nasal secretions from the prior backpassage. Seven animals were inoculated in backpassages #1, 3 and 4; 10 animals were inoculated in backpassage #2. Three animals served as non-inoculated (NT) controls for each backpassage. During backpassage #4, two inoculated (T04) calves were noted as having both mild attitude and ear droop post inoculation. Animal 5460 was scored for mild attitude on day 4 and for ear droop on days 5-7 and 9-11, and animal 5463 was scored for attitude on days 9, 10, and 11, and for ear droop on day 11. Previous safety studies with other intranasally administered *P. multocida* vaccine candidates have indicated that dropped ear may be indicative of a possible safety issue due to the ability of the vaccine strains to colonize the inner/middle ear canal. Dropped ears are also viewed unfavorably by producers in the field. The two animals were euthanized and necropsied on day 11, and subsequent bacterial culture of the left inner ear swab taken from one of the two animals (5463) was found to contain *P. multocida*. The *P. multocida* isolated from the inner ear was confirmed to be the ΔhyaC/ΔnanP vaccine strain via PCR. Due to this potential safety issue, the vaccines of the invention are preferred for administration routes other than as intranasally administered vaccine.

Example 8. Evaluation of Efficacy of ΔhyaC/nanP
*Pasteurella multocida* Vaccine when Administered
Intranasally to Young Calves The objective of the study was to determine the efficacy of two doses of a lyophilized, fermentor-grown vaccine antigen, ΔhyaC/ΔnanP *Pasteurella multocida* when administered intranasally to calves at approximately 14 days of age.

Holstein bull calves were randomly assigned to one of the following treatment groups:

T01 (Saline, intranasal; n=13);

T02 (ΔhyaC/ΔnanP *Pasteurella multocida*, Pre-vaccination: $1.13\times10^9$ CFU/dose; Post-vaccination: $1.14\times10^9$ CFU/dose, intranasal, n=20);

T03 (ΔhyaC/ΔnanP *Pasteurella multocida*; Pre-vaccination: $0.87\times10^9$ CFU/dose; Post-vaccination: $0.80\times10^9$ CFU/dose, subcutaneous, n=20);

T04 (ΔyiaO *Pasteurella multocida* at $1\times10^9$ CFU/dose, subcutaneous, n=13); (yiaO is the same gene as nanP, but there is only one deletion in this case).

Calves were vaccinated with their assigned treatment on day 0. Clinical observations and rectal temperatures were collected for all calves on days 29-36 for the T01-T04 groups. T01-T04 groups were challenged on day 30, and humanely euthanized and necropsied on day 36. At necropsy, lung swabs were collected, and lungs were scored for percent lung with lesion.

Mortality was significantly reduced in all of the vaccinate groups (T02, T03, and T04), when compared to the saline controls (T01). The intranasally vaccinated group (T02) had the greatest reduction in mortality of the two groups vaccinated with ΔhyaC/ΔnanP *P. multocida*. There were no statistically significant differences in lung lesions among the treatment groups, although lesions were numerically lower in the T02, T03, and T04 groups compared with the T01 group. These results indicate that mortality may be the preferred indicator of efficacy for this model/vaccine. Safety of the isolate was confirmed as there were only minor and sporadic clinical signs observed post-vaccination.

Example 9. Challenge Model Evaluation of *Pasteurella multocida* in Holstein Calves The objective of the study was to evaluate the severity and consistency of two challenge doses and two challenge methods of *P. multocida* (Strain 50940) in calves vaccinated subcutaneously ("SQ") at 5 weeks of age.

Sixty-four approximately 5 week old Holstein bull calves were randomly assigned (see Table 6) to one of the following treatment groups for the study: T01 (Saline, SQ, n=8); T02 ($0.8\pm0.14\times10^9$ CFU/dose *Pasteurella multocida* ΔhyaC/ΔnanP, SQ, n=8); T03 (Saline, SQ, n=8); T04 ($0.8\pm0.14\times10^9$ CFU/dose *Pasteurella multocida* ΔhyaC/ΔnanP, SQ, n=8); T05 (Saline, SQ, n=8); T06 ($0.8\pm0.14\times10^9$ CFU/dose *Pasteurella multocida* ΔhyaC/ΔnanP, SQ, n=8); T07 (Saline, SQ, n=8); T08 ($0.8\pm0.14\times10^9$ CFU/dose *Pasteurella multocida* ΔhyaC/ΔnanP, SQ, n=8). Calves were vaccinated with their assigned treatment on day 0. Blood was collected for all calves on days −1, 20, and 27. Injection site reactions, clinical observations, and rectal temperatures were collected for all calves on days −1, 1-3, 7, and 20. Additionally, clinical observations and rectal temperatures were collected for all calves on days 0 and 22 27.

Groups T01-T08 were challenged on day 21 by transtracheal challenge method. Groups T01-T02 were recumbent for the procedure and were administered $6.7\times10^8$ CFU/dose of *P. multocida*, Strain 50940. Groups T03-T04 were standing for the procedure and were administered $6.7\times10^8$ CFU/dose of *P. multocida*, Strain 50940. Groups T05-T06 were recumbent for the procedure and were administered $5.6\times10^9$ CFU/dose of *P. multocida*, Strain 50940. Groups T07-T08 were standing for the procedure and were administered $5.6\times10^9$ CFU/dose of *P. multocida*, Strain 50940. The calves were humanely euthanized and necropsied on day 27. At necropsy, lung swabs were collected, and lungs were scored for percent lung with lesion.

Lung lesions were significantly reduced in the T04 vaccinate group compared with the T03 control group. None of the other treatment comparisons (T01 vs. T02, T05 vs. T06, and T07 vs. T08) had a significant difference in lung lesions. There was no significant reduction in mortality between any of the vaccinate groups compared to their respective controls. The results of this study indicate that in 5 week old calves, lung lesions may be a better indicator of efficacy than mortality. Additionally, the data in this study also indicate that the standing route of challenge (with an approximate challenge concentration of $6.7\times10^8$ CFU/dose) may produce the best challenge results in five-week-old calves.

TABLE 6

Study Design

| Trmt Group | # of Animals | Treatment* | Challenge Method | Challenge Dose |
|---|---|---|---|---|
| T01 | 8 | Saline | Recumbent | Start: $6.7\times10^8$ CFU/dose |
| T02 | 8 | $0.8\pm0.14\times10^9$ CFU/dose *Pasteurella multocida* ΔhyaC/ΔnanP | | End: $7.1\times10^8$ CFU/dose |
| T03 | 8 | Saline | Standing | |
| T04 | 8 | $0.8\pm0.14\times10^9$ CFU/dose *Pasteurella multocida* ΔhyaC/ΔnanP | | |
| T05 | 8 | Saline | Recumbent | Start: $5.6\times10^9$ CFU/dose |
| T06 | 8 | $0.8\pm0.14\times10^9$ CFU/dose *Pasteurella multocida* ΔhyaC/ΔnanP | | End: $6.4\times10^9$ CFU/dose |
| T07 | 8 | Saline | Standing | |
| T08 | 8 | $0.8\pm0.14\times10^9$ CFU/dose *Pasteurella multocida* ΔhyaC/ΔnanP | | |

Lung Lesion Results

Lung lesions for T01-T08 groups are displayed in Table 7. Lung lesions were not significantly reduced in the T01 vs. T02, T05 vs. T06, or T07 vs. T08 groups; however, for T03 vs. T04 there was significance in reduction of lung lesions ($P\leq0.10$; Table 8). Additionally, the mitigated fraction for the T03 vs. T04 comparison was 0.63, with a 90% confidence interval of 0.188, 1.000. None of the other treatment group comparisons had a 90% lower bound that was greater than zero (Table 9).

TABLE 7

Lung Lesion Results

| Treatment Number | Back Transform LS Mean % Lung with Lesions | Standard Error % Lung with Lesions | Lower 90% Confidence Limit of Mean | Upper 90% Confidence Limit of Mean | Range % Lung with Lesions |
|---|---|---|---|---|---|
| T01 | 30 | 7 | 18 | 43 | 14 to 73 |
| T02 | 18 | 4 | 12 | 25 | 10 to 29 |
| T03 | 32 | 5 | 25 | 40 | 15 to 71 |
| T04 | 18 | 4 | 12 | 25 | 6 to 33 |
| T05 | 38 | 5 | 31 | 46 | 18 to 58 |
| T06 | 32 | 7 | 19 | 45 | 11 to 69 |
| T07 | 45 | 5 | 37 | 53 | 28 to 67 |
| T08 | 39 | 5 | 31 | 47 | 25 to 57 |

TABLE 8

P-values for Least Squares Means for Lung Lesion Contrasts

| Contrast | P-value |
|---|---|
| T01 vs. T02 | 0.1439 |
| T03 vs. T04 | 0.0234 |
| T05 vs. T06 | 0.4651 |
| T07 vs. T08 | 0.4015 |

TABLE 9

Mitigated Fractions (MF) Estimate for Lung Lesions

| Contrast | MF Estimate | 90% Bootstrap Lower Limit | 90% Bootstrap Upper Limit |
|---|---|---|---|
| T01 vs. T02 | 0.38 | −0.125 | 0.813 |
| T03 vs. T04 | 0.63 | 0.188 | 1.000 |
| T05 vs. T06 | 0.25 | −0.313 | 0.750 |
| T07 vs. T08 | 0.25 | −0.250 | 0.750 |

Example 10. Efficacy of Varying Doses of the *P. multocida* Fraction of a Combination IBR-BVD-PI3-BRSV-MH-PM Vaccine in Young Calves The objective of the study was to compare the efficacy of varying doses of the *P. multocida* fraction of an IBR-BVD-PI3-BRSV-MH-PM combination vaccine in young calves.

One hundred and thirty-seven colostrum deprived Holstein bull calves were enrolled on study. On day −8, the pre-challenge groups (NT1 through NT4) were vaccinated subcutaneously with 2 mL of their assigned (see Table 10) treatment: IBR-BVD-PI3-BRSV-MH (NT1/NT3) or IBR-BVD-PI3-BRSV-MH-PM (NT2/NT4; $2.41 \times 10^9$ CFU/dose *P. multocida*). On day 0, treatment groups T01 through T05 were vaccinated subcutaneously one of the following: T01 (IBR-BVD-PI3-BRSV-MH, n=24), T02 (IBR-BVD-PI3-BRSV-MH, n=23, $8.27 \times 10^5$ CFU/dose *P. multocida*), T03 (IBR-BVD-PI3-BRSV-MH, n=23, $8.30 \times 10^6$ CFU/dose *P. multocida*), T04 (IBR-BVD-PI3-BRSV-MH, n=24, $1 \times 10^8$ CFU/dose *P. multocida*), or T05 (IBR-BVD-PI3-BRSV-MH, n=24, $1.51 \times 10^9$ CFU/dose *P. multocida*). Injection site reactions were collected on the day prior to vaccination, for three days post-vaccination, on approximately day 7, and on the day prior to challenge. Blood was collected on days −2, 21, and 28 (−9, 13, and 20 for the NT groups), and from animals prior to euthanasia during the challenge phase. Clinical observations and rectal temperatures were recorded on days −1, 0, and 1-3 (−9, −8, and −7 through −4 for the NT groups), as well as on days 21 through 28 (13 through 20 for the NT groups). On day 22 (14 for the NT groups), animals were challenged trans-tracheally with a virulent heterologous *P. multocida* strain. Post-challenge, any animal that was euthanized or died prior to necropsy day was scored for percent lung with lesions and had lung swabs collected. On day 28 (20 for the NT groups), all remaining animals were humanely euthanized, lung lesions scored, and lung swabs collected.

The study was considered valid as all test criteria and outcome criteria were met. Mortality was significantly reduced in the T03 and T05 treatment groups compared to the T01 control group; there were no differences in lung lesions between any of the treatment groups. A potential safety issue was identified due to the anaphylactic reactions observed immediately post-vaccination in the T01 and T05 group. The reactions ranged from mild (recovered without treatment) to severe (death). The LPS content of the vaccines was tested, and all vaccines came within the range of LPS deemed accept by manufacturing for the licensed BoviShield GOLD One-Shot product (4X41.20; upper limit of 42 µg/dose). This study confirms that efficacy can be achieved with a *P. multocida* dose as low as $1 \times 10^7$ CFU/dose when dosed with the full combination of the IBR-BVD-PI3-BRSV-MH fractions. Mortality data are reported in Table 11 and Lung Lesion Data in Table 12.

TABLE 10

Study Design

| Trt Num | N | Treatment | *P. multocida* CFU/dose** | Challenge | Challenge Day |
|---|---|---|---|---|---|
| T01 | 24 | IBR-BVD-PI3-BRSV-MH | N/A | *P. multocida* ($6.5 \times 10^9$ CFU/dose) | 22 |
| T02 | 23 | IBR-BVD-PI3-BRSV-MH-PM | $8.27 \times 10^5$ | | |
| T03 | 23 | IBR-BVD-PI3-BRSV-MH-PM | $8.30 \times 10^6$ | | |
| T04 | 24 | IBR-BVD-PI3-BRSV-MH-PM | $1.00 \times 10^8$ | | |
| T05 | 24 | IBR-BVD-PI3-BRSV-MH-PM | $1.51 \times 10^9$ | | |

TABLE 10-continued

Study Design

| Trt Num | N | Treatment | P. multocida CFU/dose** | Challenge | Challenge Day |
|---|---|---|---|---|---|
| NT1* | 5 | IBR-BVD-PI3-BRSV-MH | N/A | P. multocida | 14 |
| NT2* | 5 | IBR-BVD-PI3-BRSV-MH-PM | $2.41 \times 10^9$ | ($6.5 \times 10^9$ CFU/dose) | |
| NT3* | 4 | IBR-BVD-PI3-BRSV-MH | N/A | P. multocida | |
| NT4* | 5 | IBR-BVD-PI3-BRSV-MH-PM | $2.41 \times 10^9$ | ($6.0 \times 10^8$ CFU/dose) | |

Note 1*
NT1-NT4 groups were vaccinated on day −8; T01-T05 groups were vaccinated on day 0.
Note 2**
Counts presented here are from the end of vaccination and challenge, respectively.

TABLE 11A

Mortalities/Euthanizations Post-Challenge

| | Mortality/Euthanizations | |
|---|---|---|
| Treatment Group | Number | % |
| T01 | 11/24 | 45.8 |
| T02 | 10/22 | 45.5 |
| T03 | 3/23 | 13.0 |
| T04 | 6/23 | 26.1 |
| T05 | 4/22 | 18.2 |

TABLE 11B

Mortality Contrast Comparisons (P-values)

| Contrast | P-Value |
|---|---|
| T01 vs T02 | 1.0000 |
| T01 vs T03 | 0.0243* |
| T01 vs T04 | 0.2270 |
| T01 vs T05 | 0.0625* |

TABLE 11C

Prevented Fraction (PF) Estimates for Mortality

| Contrast | PF Estimate | 90% Lower Bound Exact | 90% Upper Bound Exact |
|---|---|---|---|
| T01 vs T02 | 1. 0.8 | 2. −75.1 | 3. 46.7 |
| T01 vs T03 | 4. 71.5 | 5. 29.4 | 6. 93.7 |
| T01 vs T04 | 7. 43.1 | 8. −13.1 | 9. 77.2 |
| T01 vs. T05 | 10. 60.3 | 11. 11.9 | 12. 85.9 |

Lung lesions for the pre-challenge groups (NT1-NT4) are displayed in Table 12, and lung lesions for T01-T05 are in Table 13. None of the treatment groups showed a significant reduction in lung lesions when compared to the control (Table 6) when analyzed by p-values (p≤0.10; Table 7) or mitigated fractions (Table 14).

TABLE 12

NT1-NT4 Lung Lesions

| Trmt Group | Number of Animals | Back Transform mean % Lung with Lesions | Range % Lung with Lesions |
|---|---|---|---|
| NT1 | 5 | 39 | 26 to 62 |
| NT2 | 5 | 24 | 6 to 46 |

TABLE 12-continued

NT1-NT4 Lung Lesions

| Trmt Group | Number of Animals | Back Transform mean % Lung with Lesions | Range % Lung with Lesions |
|---|---|---|---|
| NT3 | 3 | 31 | 24 to 43 |
| NT4 | 5 | 15 | 10 to 21 |

TABLE 13

T01-T05 Lung Lesions

| Trmt Group | Number of Animals | Back Transform LS mean % Lung with Lesions | Lower 90% Confidence Limit of Mean | Upper 90% Confidence Limit of Mean | Range % Lung with Lesions |
|---|---|---|---|---|---|
| T01 | 24 | 37 | 31 | 42 | 10 to 71 |
| T02 | 22 | 39 | 33 | 45 | 15 to 81 |
| T03 | 23 | 31 | 25 | 36 | 4 to 54 |
| T04 | 23 | 31 | 26 | 37 | 9 to 69 |
| T05 | 22 | 33 | 28 | 39 | 3 to 83 |

TABLE 14

P-Values for Lung Lesion Contrasts

| Contrast | P-Value |
|---|---|
| T01 vs T02 | 0.6535 |
| T01 vs T03 | 0.215 |
| T01 vs T04 | 0.2965 |
| T01 vs T05 | 0.5051 |

Example 11. Safety Evaluation of Different Downstream Processing of P. multocida ΔhyaC/ΔnanP in Calves The objective of the study was to evaluate the safety of different downstream processing methods for use in preparing the P. multocida ΔhyaC/ΔnanP live bacterial antigen for use, for example, in two-month-old calves. It should be noted than the LPS (bacterial lipopolysaccharide)e and endotoxin burden of a combined Pasteurella multocida/ Mannheimia haemolytica composition may be too high without additional formulation steps. Forty-five, approximately two-month-old Holstein bull calves were randomly assigned to one of six treatment groups, based on the specific processing treatment of the P. multocida fraction (Table 15).

TABLE 15

Test Groups Based on Treatment Process

| Trmt Group | # of Animals | Treatment | P. multocida (CFU/dose) | M. haemolytica (RP/dose) |
|---|---|---|---|---|
| T01 | 8 | MH-PM (Current PM DSP Process) | $6.95 \times 10^9$ | 34.2 |
| T02 | 9 | PM Monovalent (Centrifuge/Wash Process) | $4.56 \times 10^9$ | N/A |
| T03 | 9 | PM Monovalent (Diafiltration/Wash Process) | $3.85 \times 10^9$ | N/A |
| T04 | 9 | MH-PM (Centrifuge/Wash Process) | $5.32 \times 10^9$ | 33.4 |
| T05 | 9 | MH-PM (Diafiltration/Wash Process) | $5.43 \times 10^9$ | 34.6 |
| NTX | 1 | N/A | N/A | N/A |

Animals (except for the NTX animal) were subcutaneously vaccinated on day 0 with 7 mL of their assigned treatment, split into two 3.5 mL doses administered on either side of the neck. Animals were observed at 30 minutes and 2-4 hours post-vaccination for adverse reactions. Daily injection site reactions, clinical observations, and rectal temperatures were collected on days 1 through 14. The T03 (Diafiltration/Wash Process; PM Monovalent) was the only treatment group observed with no post-vaccination reactions. Only one adverse reaction (1/9) was observed in the T02 group (Centrifugation/Wash Process, PM Monovalent) at 30 minutes post-vaccination; after treatment with dexmethasone, this animal returned to normal by the 2-4 hour check. The T02 and T03 group animals were all scored as normal on days 1 through 14. The T01, T04, and T05 groups all had at least two animals with a post-vaccination reaction on day 0, and at least one animal noted with a clinical sign on days 1-14. The results of this study indicate that the diafiltration/wash process is presently preferred for the modified live ΔhyaC/ΔnanP P. multocida vaccine, and this process is achieved as follows.

P. multocida culture was concentrated using a 0.2 um hollow fiber filter (GE Healthcare Hollow Fiber Part #CFP-2-E-A) to approximately 10-15× and diafiltered with 4.5-7× continuous flow 0.063% PBS Lepto Saline buffer (about 8.5 g/L sodium chloride, about 0.55 g/L dibasic anhydrous sodium phosphate and about 0.08 g/L monobasic anhydrous potassium phosphate). The final washed culture was checked for viability using standard bacterial plating methods and frozen.

The invention claimed is:

1. An attenuated *Pasteurella multocida* (*P. multocida*) bacterium wherein the *P. multocida* bacterium is attenuated by comprising a mutated hyaC gene that encodes a non-functional hyaC polypeptide having the amino acid sequence of SEQ ID NO:11 or encodes a polypeptide having an amino acid sequence at least 80% identical to the amino acid sequence of SEQ ID NO: 11 over the length of SEQ ID NO:11 that is in-common with said polypeptide; or comprising a mutated nanP gene that encodes a polypeptide unable to take-up sialic acid from growth media having the amino acid sequence of SEQ ID NO:4, or a polypeptide having an amino acid sequence at least 80% identical to the amino acid sequence of SEQ ID NO:4 over the length of SEQ ID NO:4 that is in-common with said polypeptide.

2. The bacterium of claim 1, which is assigned to a Serogroup A, B, D, E, or F.

3. The bacterium of claim 1, wherein the mutated nanP gene encodes the amino acid sequence of SEQ ID NO:4.

4. The bacterium of claim 1, wherein the mutated hyaC gene encodes the amino acid sequence of SEQ ID NO:11.

5. The bacterium of claim 1, wherein the mutated nanP gene is a polynucleotide with the nucleotide sequence of SEQ ID NO:3, or the nucleotide sequence of said polynucleotide is at least 80% identical to the nucleotide sequence of SEQ ID NO:3 over the length of SEQ ID NO:3 that is in-common with said polynucleotide.

6. The bacterium of claim 1, wherein the mutated hyaC gene is a polynucleotide with the nucleotide sequence of SEQ ID NO:12, or the nucleotide sequence of said polynucleotide is at least 80% identical to the nucleotide sequence of SEQ ID NO:12 over the length of SEQ ID NO:12 that is in-common with said polynucleotide.

7. The attenuated *P. multocida* bacterium of claim 1, wherein the bacterium is live.

8. The attenuated *P. multocida* bacterium of claim 1, wherein the bacterium is killed.

9. The attenuated *P. multocida* bacterium of claim 1, wherein the bacterium comprises a mutated hyaC gene that encodes a non-functional hyaC polypeptide having the amino acid sequence of SEQ ID NO:11, and a mutated nanP gene that encodes a polypeptide unable to take-up sialic acid from growth media having the amino acid sequence of SEQ ID NO:4.

10. An attenuated *P. multocida* bacterium comprising a hyaC gene that encodes a non-functional hyaC polypeptide having an amino acid sequence at least 80% identical to the amino acid sequence of SEQ ID NO:11 over the length of SEQ ID NO:11 that is in-common with said polypeptide, and a nanP gene that encodes a polypeptide unable to take-up sialic acid from growth media having an amino acid sequence at least 80% identical to the amino acid sequence of SEQ ID NO:4 over the length of SEQ ID NO:4 that is in-common with said polypeptide.

* * * * *